Figure 1:
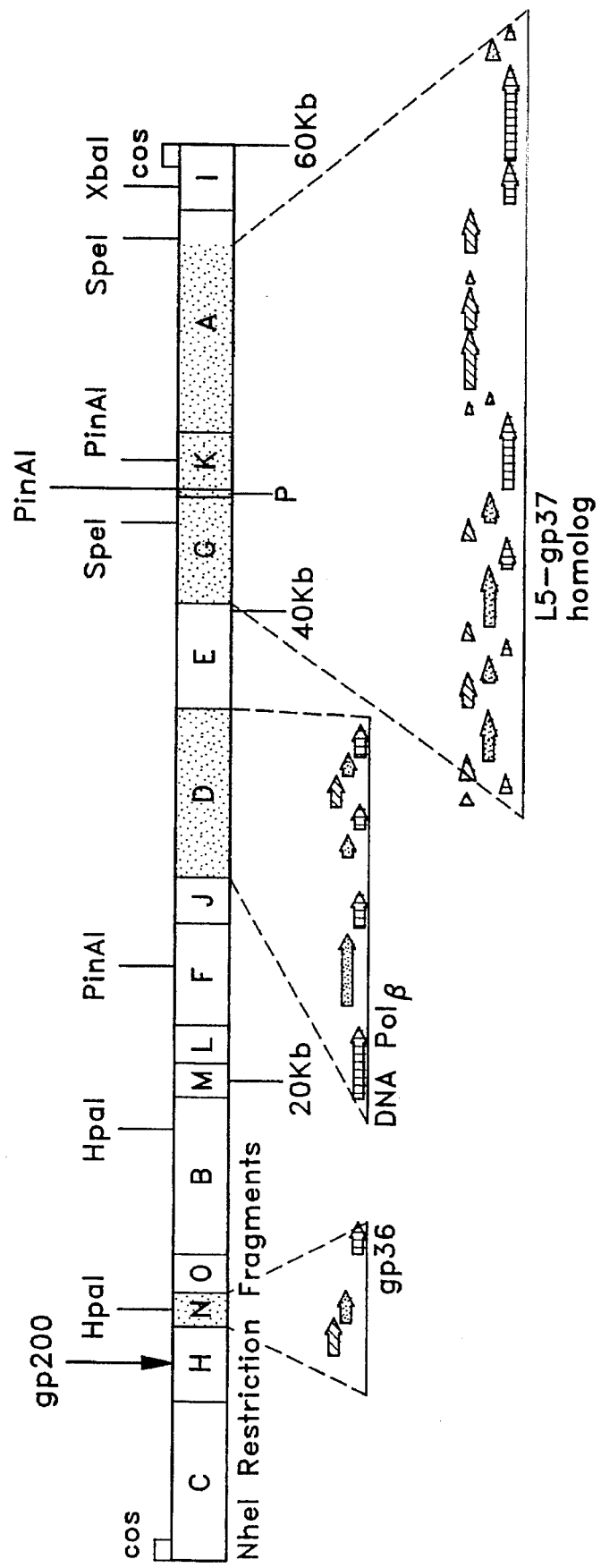

United States Patent [19]

Pearson et al.

[11] Patent Number: 5,476,768
[45] Date of Patent: Dec. 19, 1995

[54] MYCOBACTERIOPHAGE DSGA SPECIFIC FOR THE MYCOBACTERIUM TUBERCULOSIS COMPLEX

[75] Inventors: Robert E. Pearson, Durham; Julie A. Dickson, Raleigh; Paul T. Hamilton, Cary; Michael C. Little, Raleigh; Wayne F. Beyer, Jr., Bahama, all of N.C.

[73] Assignee: Becton, Dickinson and Company, Franklin Lakes, N.J.

[21] Appl. No.: 402,282

[22] Filed: Mar. 10, 1995

[51] Int. Cl.$^6$ .............. C12Q 1/68; C12P 19/34; C07H 21/02; C07H 21/04
[52] U.S. Cl. .............. 435/6; 435/91.2; 536/22.1; 536/23.1; 536/24.32
[58] Field of Search .............. 435/6, 91.2; 536/22.1, 536/23.1, 24.3, 24.32

[56] References Cited

PUBLICATIONS

Redmond et al., (1960), "A bacteriophage specific for *Mycobacterium tuberculosis*, varieties *hominis* and *bovis*", Am. Rev. Resp. Dis. 82(6):781–786.
Redmond et al., (1963), "Spotting method of phage typing mycobacteria", Am. Rev. Resp. Dis. 87:257–263.
Ross et al., (1991), "Differentiation of *Mycobacterium tuberculosis* strains by use of a nonradioactive southern blot hybridization method", J. Inf. Dis. 163:904–907.
Jones, (1988), "Bacteriophage typing of *Mycobacterium tuberculosis* cultures from incidents of suspected laboratory cross contamination" Tubercle 69:43–46.
Saunders, (1995), "State of the art: typing *Mycobacterium tuberculosis*", J. Hosp. Inf. 29::169–176.
Sula et al., (1979), "Accidental contamination of diagnostic cultures of *mycobacteria* and phage identification of the contaminating strain", Tubercle 60:159–162.
Jacobs et al., (1989), "Mycobacteriophage vector systems", Rev. Inf. Dis. 11(2):S404–S410.
Grange et al., (1978), "Host–phage relationships in the genus mycobacterium and their clinical significance", Tubercle 59:203–225.

*Primary Examiner*—W. Gary Jones
*Assistant Examiner*—Jeffrey N. Fredman
*Attorney, Agent, or Firm*—Donna R. Fugit

[57] ABSTRACT

Mycobacteriophage DS6A has been characterized and found to specifically infect all species of the TB complex, without any detectable infection of mycobacteria species other than those of the TB complex. DNA sequence analysis revealed several potential open reading frames, including one encoding a protein analogous to gp37 of mycobacteriophage L5 and a second encoding a protein with significant homology to the *S. coelicolor* DNA polymerase β subunit. Based on the DNA sequence analysis, cloning sites can be identified for insertion of reporter genes, making DS6A useful as a reporter phage for specific detection and identification of species of the TB complex.

15 Claims, 1 Drawing Sheet

MYCOBACTERIOPHAGE DSGA SPECIFIC FOR THE MYCOBACTERIUM TUBERCULOSIS COMPLEX

FIELD OF THE INVENTION

The present invention relates to characterization of mycobacteriophage, and in particular to nucleic acid sequences of mycobacteriophage.

BACKGROUND OF THE INVENTION

The Mycobacteria are a genus of bacteria which are acid-fast, non-motile, gram-positive rods. The genus comprises several species which include, but are not limited to, *Mycobacterium africanum, M. avium, M. bovis, M. bovis-*BCG, *M. chelonae, M. fortuitum, M. gordonae, M. intracellulare, M. kansasii, M. microti, M. scrofulaceum, M. paratuberculosis* and *M. tuberculosis* (M.tb). Certain of these organisms are the causative agents of disease. For the first time since 1953, cases of mycobacterial infections are increasing in the United States. Of particular concern is *M. tuberculosis,* which infects one third of the world's population and is the etiological agent of tuberculosis. Many new cases of mycobacterial infection are related to the AIDS epidemic, which provides an immune compromised population which is particularly susceptible to infection by Mycobacteria. The World Health Organization also estimates that approximately 3 million people will die from tuberculosis annually. Although effective antibiotic treatments are available for tuberculosis, the recent emergence of multiple-drug resistant strains of *M. tuberculosis* poses a serious public health concern. *M. tuberculosis* and other mycobacteria which are closely related to it (*M. bovis, M. africanum, M. bovis* BCG and *M. microti*) are referred to as the "TB complex." Mycobacterial infections caused by species other than tuberculosis are also increasing as a result of recent increases in the number of immune compromised patients. For example, *M. avium, M. kansasii* and other non-tuberculosis mycobacteria are found as opportunistic pathogens in patients infected with HIV as well as in in other immune compromised patients. These and other non-TB complex species are referred to as "mycobacteria other than tuberculosis" (MOTT).

The first isolation of a bacteriophage which infected a mycobacterium (mycobacteriophage) was reported in 1947. This mycobacteriphage infected *M. tuberculosis.* Since that time, a large number of different mycobacteriophage have been isolated and characterized. The host range of mycobacteriophage varies greatly, with some capable of infecting only a single species. Others (e.g., D29) have a very broad range of mycobacterial hosts. The different host ranges of certain mycobacteriophage have been utilized in a phage typing system for *M.* tuberculosis (Crawford and Bates. 1984. *The Mycobacteria—A Sourcebook.* Vol. 15 G. P. Kubica and L. G. Wagner, eds. Marcel Dekker, Inc., New York). In addition, the isolation and characterization of mycobacteriophage has made possible their use as cloning vectors for introducing genes into mycobacteria, in some cases species-specifically (W. R. Jacobs, et al. 1989. *Rev. Inf. Dis.* 11 (Supp. 2):S404–S410).

The recent increase in the number of clinical isolates of tuberculosis which are resistant to at least one of the antibiotics normally used to treat the disease (e.g., isoniazid, rifampin or streptomycin) has resulted in a corresponding increase in the number of fatalities in both immunocompetent and immunocompromised individuals. Because M.tb. grows very slowly (doubling time 20–24 hrs.), conventional methods for identifying this organism and determining drug susceptibility require 2–18 weeks. Conventional diagnosis of mycobacterial infections generally relies on acid-fast staining and cultivation of the organism, followed by biochemical and morphological assays to confirm the presence of mycobacteria and identify the species. These procedures are time-consuming, and a typical diagnosis using conventional culture methods can take as long as six weeks. Automated culturing systems such as the BACTEC™ system (Becton Dickinson Diagnostic Instrument Systems, Sparks, Md.) can decrease the time for detection of mycobacteria to one to two weeks. Once detected, culturing these slow-growing microorganisms in the presence of antibiotics to determine their drug susceptibility requires several additional weeks. There is still a need to even further reduce the time required for diagnosing mycobacterial infections and determining antibiotic susceptibility in order to allow prompt, informed treatment of M.tb. infections.

The BACTEC TB System provides one means for determining whether or not a positive mycobacterial culture is the result of TB complex mycobacteria or mycobacteria other than tuberculosis (MOTT). This is important information for the initial diagnosis of tuberculosis, and shortens the time required for determining the species present in a positive mycobacterial culture. The BACTEC TB identification scheme relies on a combination of three tests, namely, morphology on smear, growth characteristics and the NAP (p-nitro-α-acetylamino-β-hydroxy-propiophenone) TB differentiation test. To improve identification of TB complex species, it is highly desirable to shorten the length of time required to perform such distinguishing tests.

Of particular interest in this regard is the recent development of a diagnostic assay employing recombinant mycobacteriophage. The cDNA encoding firefly luciferase (FFluc) has been inserted into the genomes of mycobacteriophage for use as a reporter gene in antibiotic susceptibility testing of mycobacteria, i.e., as an in vivo measure of cell viability after exposure to antibiotics. W. R. Jacobs, et al. (1993) *Science* 260:819 and WO 93/16172. Luciferase is useful as a biological reporter or signal generating molecule because it catalyzes the reaction of luciferin with adenosine triphosphate (ATP), resulting in the production of light. Inhibition of culture growth results in reduced or absent light production from the cloned luciferase gene. This effect has been attributed to reduced amounts of ATP (required for the luciferase reaction) in antibiotic-sensitive cells, which exhibit reduced metabolic activity in the presence of an anti-mycobacterial antibiotic, but many other metabolic functions may be affected as well.

Certain mycobacteriophage (e.g., TM4 or phAE40) have been characterized as preferentially infecting species of the TB complex. However, none of these phage are perfectly TB complex-specific and are capable of efficiently infecting certain MOTT species as well. As a result, reporter mycobacteriophage constructed in, for example, TM4 also produce high levels of signal in certain MOTT species. This produces false-positives which are unacceptable for clinical detection and identification of TB complex mycobacteria. A reporter mycobacteriophage which is truly specific for TB-complex organisms is therefore highly desirable for development of a useful diagnostic test.

Mycobacteriophage DS6A was originally isolated from stockyard soil by W. B. Redmond and J. C. Cater (1960. *Amer. Rev. Resp. Dis.* 82:781–786). They found that DS6A was lytic on *M. tuberculosis* and *M. bovis* strains but did not lyse any other mycobacterial strain tested. Based on its unique host range, DS6A was included in the Mycobacterial Typing Phage panel for typing and epidemiological analysis of *M. tuberculosis* isolates. DS6A has subsequently been tested on over 8,000 strains of *M. tuberculosis* and *M. bovis* and never failed to form plaques. A few strains of *M. africanum* have also been tested and found to be infected by DS6A. While DS6A was previously known primarily as an *M. tuberculosis* and *M. bovis*-specific phage, its ability to infect other TB complex species and the degree of TB-complex specificity has never been fully determined. The present invention, by virtue of the discovery that DS6A is truly specific for TB complex mycobacteria, for the first time allows specific detection of TB complex species in a reporter mycobacteriophage (RM) assay. No truly TB-complex-specific mycobacteriophage were previously known, so it was unexpected that the full host range testing described herein would reveal this property in DS6A. Use of DS6A as a reporter mycobacteriophage therefore provides a truly TB complex-specific diagnostic test, eliminates the false-positives of prior art RM assays for TB complex mycobacteria and provides more accurate identification of TB complex organisms using a reporter mycobacteriophage.

As used herein, the term "reporter gene" refers to a gene which can be expressed to produce a gene product which directly or through further reaction generates a detectable signal. Infected cells are detected by means of the reporter gene signal associated with the infected cells. This signal can be used to detect or identify cells carrying the reporter gene, either on a plasmid or inserted into the genome of the cell. Many reporter genes are known in the art, as are methods for using their expression to generate a detectable signal. Examples of reporter genes known in the art are the gene encoding firefly luciferase (resulting in a luminescent signal upon reaction with luciferin) and the gene encoding β-galactosidase (resulting in a colored or fluorescent signal upon reaction with appropriate enzyme substrates). A mycobacteriophage carrying a reporter gene is referred to herein as a "reporter mycobacteriophage" or "RM."

SUMMARY OF THE INVENTION

Mycobacteriophage DS6A has been found to specifically infect all species of the TB complex, without any infection of MOTT species detected. In its physical characteristics, DS6A strongly resembles many other mycobacteriophage, having an isometric head and a long, non-contractile tail. The phage particle is composed of at least two major structural proteins. Genetic analysis revealed that the genome is an approximately 60 Kd double-stranded DNA molecule with cohesive ends and 69% G+C content. The DNA sequence of 40% of the genome was determined and thirty-five potential open reading frames were identified. A search of the GENBANK database revealed no significant similarities between the DNA sequences determined for DS6A and any other DNA sequences. However, the protein encoded by one of the open reading frames showed identity with gp37 of mycobacteriophage L5 and the protein encoded by a second open reading frame showed significant homology to the *Streptomyces coelicolor* DNA polymerase beta subunit. The unique TB-complex specific host range of DS6A and the present characterization of its genome make this mycobacteriophage useful for the detection and identification of TB-complex mycobacteria.

DESCRIPTION OF THE DRAWINGS

FIG. 1 illustrates the restriction map of DS6A, including the sites of potential open reading frames and the regions encoding several DS6A proteins.

DETAILED DESCRIPTION OF THE INVENTION

Host range of DS6A

A method similar to the test dilution method of phage typing described by W. B. Redmond et al. (1963. *Amer. Rev. Resp. Dis.* 87:257–263) was used to determine the host range of mycobacteriophage DS6A. Test host bacteria were grown to an $A_{600}$ of approximately 1.0 in Middlebrook 7H9 broth (BBL) supplemented with 0.2% glycerol, 10% ADC (5% BSA, 2% dextrose, 145 mM NaCl) and 0.05% TWEEN 80. Cells were pelleted at 5000xg for 10 minutes, washed twice in 7H9 broth supplemented with 10% ADC, and then resuspended in their original volume. To prepare bacterial lawns, 0.5 ml of slow-growing organisms or 0.3 ml of fast-growing organisms were added to 3 ml top agar (7H9 broth supplemented with 10% ADC and 7.5 g/l Noble agar) and poured onto 7H10 plates supplemented with 0.5% glycerol and 10% ADC. DS6A phage stocks were diluted into MP buffer (10 mM Tris-HCl, pH 8; 100 mM NaCl; 10 mM $MgSO_4$; 2 mM $CaCl_2$). Ten μl of each dilution, containing 10, 100, or 1000 pfu of DS6A, were spotted onto lawns of the test host bacteria and the plates were incubated at 37° C. in a humidified incubator for 1–7 days, until zones of lysis were visible as an indication of successful infection.

Table 1 shows the results of the host range testing of DS6A. DS6A was found to form plaques only on *M. tuberculosis, M. bovis, M. bovis* BCG, *M. africanum* and *M. microti.* Drug-resistant as well as drug-sensitive strains of *M. tuberculosis* were susceptible to DS6A infection, as were both clinical isolates and lab strains. No plaques were formed on any other mycobacterial species tested or on *Rhodococcus sp., Pseudomonas aeruginosa,* or *Nocardia asteroides.*

TABLE 1

| | | Host Range Testing of DS6A | | | |
|---|---|---|---|---|---|
| Mtb complex | RTD | MOTT | RTD | Other | RTD |
| M. tb 201 | + | *M. kansasii* | − | Rhodococcus sp. | − |
| M. tb 303 | + | *M. intracellulare* | − | *Pseudomonas aeruginosa* | − |
| M. tb-rif$^r$ | + | *M. avium* 1499 | − | *Nocardia asteroides* | − |
| M. tb 301 | + | *M. avium* 1225 | − | | |
| M. tb-ethamb$^r$ | + | *M. avium* 1546 | − | | |
| M. tb 509 | + | *M. avium* 1408 | − | | |
| M. tb 554 | + | *M. gordonae* | − | | |
| M. tb 1571 | + | *M. chelonae* | − | | |
| M. tb 1476 | + | *M. fortuitum* | − | | |
| M. tb 790 | + | *M. smegmatis* | − | | |
| *M. bovis* | + | *M. szulgai* | − | | |
| *M. bovis* BCG | + | *M. xenopii* | − | | |

TABLE 1-continued

Host Range Testing of DS6A

| Mtb complex | RTD | MOTT | RTD | Other | RTD |
|---|---|---|---|---|---|
| M. africanum | + | M. scrofulacium | − | | |
| M. microti | + | M. flavescens | − | | |
| | | M. terrae | − | | |

(+) indicates zone of lysis; (−) indicates no lysis due to phage.

Characterization of DS6A phage particles

Electron micrographs of DS6A phage particles revealed an isometric head with a hexagonal outline (700–800 Å from point to point) and a long, flexible, non-contractile tail (2000–2900 Å in length). The tail ended in a baseplate with at least two long tail fibers extending from it. These tail fibers probably play a significant role in the species-specificity of the phage. The morphology established DS6A as member of the Siphoviridae family of bacteriophage, morphotype B1.

SDS-PAGE analysis of DS6A phage particles showed two major structural proteins with molecular masses of about 36.5 Kd and 200 Kd. Several minor proteins were also observed. By analogy to other mycobacteriophage, the 36.5 Kd and the 200 Kd DS6A proteins are believed to be the major tail subunit and the major head subunit proteins. N-terminal sequence analysis of the 36.5 Kd DS6A protein (referred to herein as gp36) yielded the sequence: ANAKNIYAAEPTAXGSIDAQPG (SEQ ID NO:4). The gene encoding this protein has been identified in the DS6A genome and partially sequenced (see below). The N-terminus of the 200 Kd DS6A protein (referred to herein as gp200) was also sequenced and determined to be ADVS-RNDVATLIQEAYGDDFLSWAAKQS (SEQ ID NO:5). The region of the DS6A genome which encodes the gp200 protein has also been identified on the NheI-H fragment. A search of the protein sequence databanks did not identify any sequences homologous to the gp36 and gp200 N-terminal sequences. A 55 kd protein was also identified and sequencing of the N-terminus yielded the sequence IVIER-GDIPSLVXRGXRLH (SEQ ID NO:6). The function of this protein is unknown. It is believed to be a DS6A protein, but this has not been conclusively demonstrated by mapping it to the genome.

Purified DS6A was used to immunize rabbits using conventional techniques. The antisera produced recognized the DS6A phage particle and bound to both gp36 and gp200 on Western blots. gp36 and gp200 are therefore phage surface proteins, although additional functions have not been ruled out. Hybridomas producing monoclonal antibodies which recognize the DS6A phage particle may also be isolated from DS6A immunized mammals using conventional methods. Labeled antibodies (either polyclonal antisera or monoclonal antibodies) produced in this manner are useful for specific detection or identification of DS6A by binding of the labeled antibody to the phage. As antibodies which recognize gp36 and gp200 have been identified in anti-DS6A antisera, these proteins may also be used as immunogens to generate polyclonal antisera to gp36 or gp200, and for generation of hybridomas which produce monoclonal antibodies specific for each of these DS6A proteins. Anti-gp36 and anti-gp200 antibodies (either polyclonal or monoclonal) may also be labeled and used to detect or identify DS6A phage, or to detect or identify the gp36 or gp200 proteins (e.g., in Western blots), by binding of the labeled antibody to the antigen.

It is generally known that the infection specificity of bacteriophage is determined by the tail proteins, which specifically attach to receptors on the surface of the bacteria which the bacteriophage infect. The specificity of DS6A for infection of species of the TB complex and identification of the tail fiber proteins will allow use of this protein as a TB complex specific tracer ligand for detection and/or identification of TB complex mycobacteria. By attaching a detectable label to the tail fiber proteins using methods known in the art for labeling proteins, a tracer protein can be prepared which binds specifically to mycobacterial cells belonging to the TB complex. The bound protein can then be detected by means of the signal associated with the attached label, thereby identifying the mycobacterium as a member of a TB complex species. The labeled tail fiber protein, by virtue of the specificity for receptors on TB complex mycobacteria, will not bind to the cells of MOTT and no signal will be detected, thereby identifying these mycobacteria as non-TB complex species, i.e., MOTT.

The DS6A phage itself may also be labeled and used for specific detection of TB complex mycobacteria. A detectable label such as biotin or a fluorescent moiety may be linked to reactive groups on the surface of the phage using coupling methods known in the art. After purification of the labeled phage, it may be used in assays in which the label carried by the phage is detected associated with phage-infected mycobacteria. The label may be either directly or indirectly detected as is known in the art. For example, biotin coupled to the phage may be detected indirectly by binding to labeled avidin, whereas a fluorescent label may be detected directly by excitation light of the appropriate wavelength.

Characterization of DS6A DNA

The *M. bovis* BCG cells were used for CsCl purification of DS6A. DS6A was deposited with the American Type Culture Collection (Rockville, Md.) as Accession No. 97076 on Mar. 2, 1995. Procedures for DS6A DNA isolation were derived from protocols published by Sambrook et al (1989. *Molecular Cloning—A Laboratory Manual.* Cold Spring Harbor Laboratory Publishers, Cold Spring Harbor, N.Y.) Confluent plate lysates of DS6A grown on *M. bovis* BCG ATCC #353734 were eluted three times with phage elution buffer (10 mM Tris pH 7.5, 25 mM NaCl, 10 mM $MgSO_4$, 1.0 mM $CaCl_2$). Eluted material was filtered through a 0.45 micron filter. Two CsCl gradient procedures were used to purify DS6A DNA from the eluted material. In one protocol, the phage were concentrated by centrifugation at 22,000 rpm for 1.5 hrs in a Type 35 rotor at 4° C. The phage pellets were resuspended overnight in Middlebrook 7H9 and 1 mM $CaCl_2$. CsCl was added to the resuspended phage (1 gm CsCl per 1 ml of phage suspension). The mixture was layered over a CsCl step gradient with CsCl layers of 1.7 gm/ml, 1.5 gm/ml, and 1.45 gm/ml. The step gradient centrifugation was performed in an SW 41 rotor for 2 hrs at 22,000 rpm at 4° C. The second protocol for CsCl isolation of DS6A DNA was that described by Jacobs et al, 1991. *Mtds. Enz.* 204:537–555. Phage bands were identified, extracted and dialyzed against phage extraction buffer. DS6A DNAs were isolated by treating the phage concentrates with 20 mM EDTA pH 8.0, 0.5% SDS, and 200 µg/ml Proteinase K overnight at 57° C. The phage lysates were extracted with phenol saturated with 50 mM Tris pH 8.0. The interface was removed and re-extracted once with 24:1 chloroform/isopropanol. The DNA was precipitated with 0.3M sodium acetate pH 7.0 and two volumes of ethanol for 30 min. at room temperature, followed by centrifugation. The pellets were washed with 70% ice cold ethanol.

Isolated DS6A genomic DNA was labelled and used to probe a Southern Blot of various mycobacteriophage DNAs under moderate stringency conditions (approximately 60–70% minimal homology). DS6A did not hybridize to DNA from any of the mycobacteriophage tested (L5, D34, AG1, or coliphage lambda). The DS6A genome is therefore useful for distinguishing this mycobacteriophage from others by DNA hybridization and for identifying DS6A in mycobacteriophage preparations. Further, there is precedent in other mycobacteriophage for lysogeny. DS6A-lysogenized TB complex mycobacteria may therefore be identified by hybridization with DS6A nucleic acid probes.

Ten ng of CsCl purified DNAs were separated by CHEF gel electrophoresis (BioRad, Richmond Calif.) with size separation from 5 Kb to 120 Kb. The 5 Kb ladder from BioRad and the high molecular weight standard from Life Technologies (Gaithersburg, Md.) were used as standards. The DS6A genome has an apparent molecular weight of about 60 Kb, based on its mobility in a 1% agarose CHEF gel. This is slightly larger than the genomes of the mycobacteriophage L5 (52 Kb), D29 (50 Kb). and AG1 (50 Kb). The size determined by CHEF gel analysis is in general agreement with the 63.3 Kb size determined by summation of the sizes of the NheI restriction fragments (Table 2).

TABLE 2

DS6A NheI Fragments

| NheI fragment | Size (Kb) | NheI fragment | Size (Kb) |
| --- | --- | --- | --- |
| A | 10.0 | I | 3.0 |
| B | 7.2 | J | 2.7 |
| C | 7.0 | K | 2.2 |
| D | 6.6 | L | 2.0 |
| E | 4.8 | M | 1.8 |
| F | 4.5 | N | 1.7 |
| G | 4.4 | O | 1.6 |
| H | 3.2 | P | 0.4 |
| Total = 63.3 Kb | | | |

A large number of restriction enzymes were initially tested for their ability to digest DS6A DNA. XbaI, PinAI, HpaI, and SpeI were found to restrict the DNA at a limited number of sites. Double digests were performed to construct a restriction map of the DS6A genome (FIG. 1). Restriction digests of DS6A DNA with SpeI or HpaI showed variable patterns depending on whether or not the DNA was heated to 65° C. prior to gel electrophoresis. Heating the DNA to 65° C. increased the intensity of the 4 Kb SpeI fragment and the 10 Kb HpaI fragment, suggesting cohesive ends on the molecule. Ligation of DS6A DNA prior to restriction eliminated the 4 Kb SpeI fragment and the 10 Kb HpaI fragment, confirming the presence of cohesive ends on the DS6A genome. The DS6A termini are therefore suitable for cosmid cloning and for construction of cosmid vectors.

DNA sequence analysis

DS6A mycobacteriphage were grown for DNA sequence analysis as described by Jacobs, et al. *Methods In Enzymology* 204:537 (1991). The NheI fragments of DS6A DNA were cloned into the XbaI site of pUC18 (Pharmacia). The SpeI fragment of DS6A was cloned into the XbaI site of pGEM 7+ (Promega) as described by J. Sambrook, et al, supra. Restriction digests and cloning procedures were also as described by Sambrook, et al. Sequencing was performed by Lark Sequencing Tech. Inc. using standard techniques. All fragments were subcloned and nested deletions of the fragments were generated by Exo III and S1 nuclease digestion. Sequencing reactions were performed with $^{35}$S-dATP and 7-deaza dGTP. 7-deaza dITP was used as necessary to resolve severe GC band compressions. All sequencing reactions were analyzed on 6% denaturing gels. Internal primers were synthesized and used as needed to confirm junction sequences.

The DNA sequence of 24,036 bases was determined, representing three different segments of the DS6A genome: 15,664 bases containing the 12 Kb SpeI fragment plus the sequence of the overlapping NheI fragment G (referred to herein as the NheI-G/SpeI fragment, see FIG. 1); 6611 bp NheI fragment D located roughly in the middle of the DS6A genome, and NheI fragment N (1761 bp). These fragments were cloned and the recombinant DNA molecules comprising the fragments were deposited with the American Type Culture Collection, Rockville, Md., as follows: the 12 Kb SpeI fragment (ATCC No. 970715, deposited on Mar. 2, 1995; NheI-G (ATCC No. 97074, deposited on Mar. 2, 1995); NheI-D (ATCC No. 97072, deposited on Mar. 2, 1995); NheI-N (ATCC No. 97073, deposited on Mar. 2, 1995). As the NheI-G/SpeI fragment sequence (SEQ ID NO:3) is a composite of the separate sequences of the two fragments, the NheI-G clone and the 12 Kb SpeI clone were deposited separately. The overall G+C content of the DS6A DNA sequence was determined to be 69%. However, within the 15.6 Kb segment, there is a 48 bp stretch (nucleotides #14615–14662) with only 25% G+C content. This A/T-rich region may represent a recognition sequence or possibly an origin of replication.

A number of open reading frames (ORF) were identified in the 24 Kb DNA sequence (Table 3). ORFs were identified based on the following criteria: The ORF starts with an ATG or GTG initiation codon, is at least 200 bp in length, and exhibits a codon preference which is similar to the codon preference found in mycobacteriophage L5 (G. F. Hatfull and G. J. Sarkis *Molec. Microbid.* 7:395–405 (1993). The potential initiation codon for each ORF was determined based on the presence of a potential ribosome binding site preceding an ATG or GTG. A potential ribosome binding site was identified as three contiguous bases positioned 2 to 12 bases from the potential initiatior codon and complementary to the 3' end of *M. bovis* 16S rRNA. SEQ ID NO:1, SEQ ID NO:2 and SEQ ID NO:3 each represent the coding strand.

TABLE 3

DS6A Open Reading Frames

| | Start | End | Length |
| --- | --- | --- | --- |
| NheI-N Fragment (SEQ ID NO:1) | | | |
| ORF 1 | 402 | 734 | 333 |
| ORF 2 | 737 | 1039 | 303 |
| ORF 3 (gp36) | 1456 | end | 303 |
| NheI-D Fragment (SEQ ID NO:2) | | | |

TABLE 3-continued

DS6A Open Reading Frames

|  | Start | End | Length |
|---|---|---|---|
| ORF 1 (DNA pol) | 390 | 1538 | 1149 |
| ORF 2 | 2107 | 3132 | 1026 |
| ORF 3 | 3138 | 3359 | 222 |
| ORF 4 | 4690 | 5028 | 339 |
| ORF 5 | 5028 | 5375 | 348 |
| ORF 6 | 5375 | 5653 | 279 |
| ORF 7 | 5653 | 5910 | 258 |
| ORF 8 | 6078 | 6491 | 414 |
| 15.6 Kb Fragment (SEQ ID NO:3) | | | |
| ORF 1 | 222 | 425 | 204 |
| ORF 2 | 451 | 747 | 297 |
| ORF 3 | 747 | 1109 | 363 |
| ORF 4 | 1109 | 2014 | 906 |
| ORF 5 | 2034 | 2747 | 714 |
| ORF 6 | 2747 | 3109 | 363 |
| ORF 7 | 3109 | 3444 | 436 |
| ORF 8 | 3444 | 3728 | 285 |
| ORF 9 | 3731 | 4855 | 1125 |
| ORF 10 (L5 gp37) | 4855 | 5376 | 522 |
| ORF 11 | 5382 | 5747 | 366 |
| ORF 12 | 5837 | 6307 | 471 |
| ORF 13 | 6403 | 7770 | 1368 |
| ORF 14 | 7770 | 8006 | 237 |
| ORF 15 | 8033 | 8236 | 204 |
| ORF 16 | 8244 | 9443 | 1200 |
| ORF 17 | 9450 | 10244 | 795 |
| ORF 18 | 10371 | 10586 | 216 |
| ORF 19 | 11115 | 11786 | 672 |
| ORF 20 | 11917 | 12741 | 825 |
| ORF 21 | 12748 | 14499 | 1752 |
| ORF 22 | 14771 | 15154 | 384 |
| ORF 23 | 15154 | 15426 | 273 |
| ORF 24 | 15429 | end | |

(ORF nucleotide positions correspond to the attached Sequence Listing)

Of course, other open reading frames may be identified within these sequences as is known in the art (e.g., GENEWORKS from Intelligenetics) by shifting the reading frame and/or modifying the criteria for the open reading frame (e.g., the length of the translation product or the ribosomal binding site).

Within the 15.6 Kb DNA fragment, all of the open reading frames would be transcribed in one direction. These ORF's appear to be closely spaced in a head-to-tail arrangement of the genes. In several cases, the initiation codon of a gene is overlapped by the termination codon of the preceding ORF. This organization suggests that the genes of the 15.6 Kb fragment are transcribed as a single operon, which is common in bacteriophage. The sequence on the NheI fragment D also contained several ORF's. All of the identified ORF's are translated in the same direction.

NheI fragment N hybridized with a degenerate probe based on reverse translation of the N-terminal sequence of the gp36 DS6A structural protein. A sequence which encodes a protein with an N-terminal sequence (minus the initator Met) identical to the N-terminal sequence of the gp36 structural protein was identified upon sequence analysis of NheI fragment N. As the entire gene is not contained on NheI fragment N, it was not possible to compare predicted molecular mass and observed molecular mass of the protein, however, this is believed to be the gp36 protein gene. ORF3 of NheI fragment N can therefore be cloned into a recombinant expression vector as is known in the art, and expressed in a transformed or transfected host cell to produce recombinant gp36. This expression product represents a portion of the gp36 protein which is useful for immunization and production of polyclonal and monoclonal anti-gp36 antibodies for detection and identification of DS6A or gp36 in immunoassays. If it is desired to express the entire gp36 gene, the remainder of the gp36 coding sequence can be isolated from adjacent fragment NheI-O as is known in the art.

A degenerate probe based on reverse translation of the gp200 structural protein hybridized to the terminal 10 Kb HpaI fragment and NheI fragment H of DS6A. NheI fragment H is adjacent to NheI fragment N on the DS6A genome. It therefore appears that the genes encoding the major structural proteins of DS6A are clustered and contained on adjacent NheI fragments N and H, approximately 9 Kb from the left end of the DS6A genome. The segment of the DS6A genome containing the gp200 coding sequence can also be isolated, cloned in an expression vector, and expressed in a transformed or transfected host cell to produce recombinant gp200 useful for production of polyclonal and monoclonal anti-gp200. As described above, such antibodies can be used in immunoassays for detection and identification of DS6A or gp200.

The DS6A DNA sequences will be useful in a variety of diagnostic and genetic systems. First, DS6A DNA can be used to construct a DS6A reporter mycobacteriophage for specific infection and detection of TB complex mycobacteria, for example as a diagnostic in clinical samples. As described above, such RM are useful for evaluation of antibiotic resistance and DS6A RM in particular will be useful for identifying TB complex mycobacteria. To produce such a DS6A RM, an expression cassette including a promoter and reporter gene may be inserted into the unique BclI site located in the SpeI fragment. The SpeI fragment is a subfragment of the 15.6 Kb DNA fragment. After insertion of the expression cassette into the cloned fragment, the expression cassette may be inserted into the DS6A genome by in vitro DNA ligation, or by in vivo recombination between the DS6A genome and the cloned SpeI fragment within a mycobacterial cell. In vivo recombination is generally accomplished by allowing mycobacteria carrying the plasmid with the expression cassette to recombine with superinfecting DS6A phage during replication of the viral DNA, resulting in a recombinant DS6A RM carrying an expressible reporter gene. Alternatively, an expression cassette may be directly cloned into a restriction site of the DS6A genome, for example, the XbaI site.

DS6A may also be adapted as a delivery phage for introduction of DNA sequences into TB complex mycobacteria. These include, for example, transposons for mutagenesis or antibiotic resistance genes. These DNA sequences may also be inserted into the DS6A genome using any of the methods described above. DS6A DNA sequences may also be used to enhance the expression of heterologous proteins in mycobacteria. As the DNA sequences of mycobacteriophage are responsible for over-expression of viral proteins during infection, these sequences will also be useful for enhancing over-expression of reporter molecules or other heterologous proteins. Such expression enhancing sequences may be identified by inserting fragments of the sequenced DNA upstream of a DNA sequences encoding a reporter molecule (e.g., luciferase or β-galactosidase) and in a screening assay identifying those fragments which result in enhanced protein production (i.e., an increase in signal). Expression enhancing sequences identified in this screening assay may then be transferred using standard recombinant techniques to positions upstream of other genes for which it is desired to enhance expression. Over-expression of proteins may be particularly useful for improving the mycobacterial vaccine strain BCG.

The DS6A genome also contains an origin of DNA replication which functions in mycobacteria. In a screening assay similar to that used to identify expression-enhancing sequences, DNA fragments containing origins of replication may be identified by cloning fragments of DS6A DNA into plasmids with a selectable marker such as an antibiotic resistance gene. Upon transforming bacteria with the plasmid and culturing in the presence of the antibiotic, only those plasmids containing an origin of replication will replicate, allowing the transformed bacterium to grow and survive in the presence of the antibiotic.

DNA homology searches

Searches for DNA sequence homologies were performed in the Genbank and EMBL DNA libraries and using Intelligenetics IG software (Intelligenetics Inc., Minnetonka, Minn.) on a VAX 9000. Homologies identified were analyzed using software programs from the FASTA/TFASTA and IFASTN package. No significant homologies were found at the DNA level with any entries in these databases. Direct comparison with the L5 DNA sequence also failed to reveal homology. Homologies to protein entries in the SwissProt, PIR, EMBL, and Genbank libraries were identified by searching with open reading frame files of the DNA sequence and with files created by generating six different reading frames for the entire DNA sequence. Potential matches were further analyzed using the FASTA and TFASTA software.

One potential open reading frame identified in DS6A (ORF 10 of the 15.6 Kb fragment) was aligned with the gp37 ORF from mycobacteriophage L5. There was approximately 60% identity over 112 amino acids. The amino terminus of L5 gp37 aligned with the internal and C-terminal portion of DS6A ORF 10 (15.6 Kb), assuming translation of the ORF 10 protein begins at the ATG at nucleotide 4855. No other genes mapping near gp37 in L5 were identified near ORF 10 (15.6 Kb) even with very weak criteria for homology. ORF 10 (15.6 Kb) appears to be a homolog of the L5 phage gp37 protein. The function of gp37 is unknown, however, it is a potential cloning site. ORF 10 (15.6 Kb) is therefore a promising site for construction of reporter mycobacteriophage in DS6A.

A second potential open reading frame ORF (ORF 1 of NheI-D) was aligned with the DNA polymerase III β-subunit of *Streptomyces coelicolor*. The polymerase III β subunit is the product of the *S. coelicolor* dnaN gene. The alignment showed significant homology of 35% over 360 amino acids. It is likely that translation of ORF 1 (NheI-D) begins at the valine GTG initiator at nucleotide 390. Use of these sequences for translation allows good alignment of both the amino and C-terminal portions of the proteins. ORF 1 (NheI-D) also shows weaker homology to the analogous proteins from *E. coli* and *B. subtilis*, probably as a result of the closer phylogenetic relationship between mycobacteria and streptomyces than between mycobacteria and *E. coli* or *B. subtilis*. However, class III-type DNA polymerases were previously unknown in phage. Phage polymerases are either of type I (Taq, klenow, L5 phage, T coliphages) or of type II (phi29). The type III enzymes are multisubunit enzymes previously found only in bacteria where they are known to be involved in DNA replication and repair. The beta subunit is not known to catalyze DNA replication by itself, but instead appears to play a role as a DNA clamp which provides processivity. Thus, if ORF 1 (NheI-D) is a bona fide DNA polymerase subunit, the other subunits might reside in the DS6A genome, or be supplied by the host cell. The highly processive nature of class III DNA polymerases makes them desirable for use in vitro in nucleic acid amplification and DNA syntheses, etc. ORF 1 (NheI-D) of DS6A may therefore be cloned and expressed in transformed host cells to produce a new recombinant class III DNA polymerase useful in these methods.

What is claimed is:

1. Isolated and purified genomic DNA of mycobacteriophage DS6A consisting of ATCC deposit #97076 further comprising SEQ ID NOs: 1 to 3 and exact complements of SEQ ID NOs: 1 to 3.

2. NheI fragment D of mycobacteriophage DS6A genomic DNA consisting of SEQ ID NO:2 or exact complement of SEQ ID NO:2.

3. NheI fragment N of mycobacteriophage DS6A genomic DNA consisting of SEQ ID NO:1 or exact complement of SEQ ID NO:1.

4. Fragment NheI-G/SpeI of mycobacteriophage DS6A genomic DNA consisting of SEQ ID NO:3 or exact complement of SEQ ID NO:3.

5. Open reading frame 1 of NheI fragment D of mycobacteriophage DS6A genomic DNA consisting of nucleotides 390 to 1538 of SEQ ID NO:2.

6. A recombinant expression vector comprising nucleotides 390 to 1538 of SEQ ID NO:2 which is the NheI fragment D of mycobacteriophage DS6A genomic DNA.

7. The recombinant expression vector of claim 6 contained in a transformed or transfected host cell.

8. Open reading frame 3 of NheI fragment N of mycobacteriophage DS6A genomic DNA consisting of nucleotides 1456 to 1761 of SEQ ID NO:1 or exact complement of nucleotides 1456 to 1761 of SEQ ID NO:1.

9. A recombinant expression vector comprising nucleotides 1456 to 1761 of SEQ ID NO:1 or exact complement of nucleotides 1456 to 1761 of SEQ ID NO:1 which is the NheI fragment N of mycobacteriophage DS6A genomic DNA.

10. The recombinant expression vector of claim 9 contained in a transformed or transfected host cell.

11. A recombinant vector comprising NheI fragment D of mycobacteriophage DS6A genomic DNA which consists of SEQ ID NO:2 or exact complement of SEQ ID NO:2.

12. A recombinant vector comprising NheI fragment N of mycobacteriophage DS6A genomic DNA which consists of SEQ ID NO:1 or exact complement of SEQ ID NO:1.

13. A recombinant vector comprising fragment NheI-G of mycobacteriophage DS6A genomic DNA which consists of ATCC deposit #97074.

14. A recombinant vector comprising fragment 12 Kb SpeI of mycobacteriophage DS6A genomic DNA which consists of ATCC deposit #97075.

15. A method for detecting DS6A mycobacteriophage comprising the steps of a) hybridizing labeled DS6A genomic DNA consisting of ATCC deposit #97076 further comprising SEQ ID NOs: 1 to 3 or exact complements of SEQ ID NOs: 1 to 3 to mycobacteriophage nucleic acids under moderate stringency conditions b) detecting the DS6A mycobacteriophage.

* * * * *

UNITED STATES PATENT AND TRADEMARK OFFICE
CERTIFICATE OF CORRECTION

PATENT NO. : 5,476,768

DATED : December 19, 1995

INVENTOR(S): Robert E. Pearson, Julie A. Dickson, Paul T. Hamilton, Michael C. Little and Wayne F. Beyer, Jr.

It is certified that error appears in the above-identified patent and that said Letters Patent is hereby corrected as shown below:

On the title page, item [54] and column 1, line 1, change "DSGA" to --DS6A--.

Signed and Sealed this

Nineteenth Day of March, 1996

Attest:

BRUCE LEHMAN

Attesting Officer     Commissioner of Patents and Trademarks

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 1761 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: misc_feature
        ( B ) LOCATION: 402..734
        ( D ) OTHER INFORMATION: /function="potential open reading frame"

( i x ) FEATURE:
        ( A ) NAME/KEY: misc_feature
        ( B ) LOCATION: 737..1039
        ( D ) OTHER INFORMATION: /function="potential open reading frame"

( i x ) FEATURE:
        ( A ) NAME/KEY: misc_feature
        ( B ) LOCATION: 1456..1761

(D) OTHER INFORMATION: /function="coding sequence"
 / product="gp36"

(xi) SEQUENCE DESCRIPTION: SEQ ID NO:1:

| | | | | | | |
|---|---|---|---|---|---|---|
| TCTAGCAACA | CGCGCAGACG | TGGCCGCCCG | CATGGGCGGC | GAACTGGACA | ACGAAACGGA | 60 |
| CGTGGCCGAC | CTGCTGGACG | AGGCCGCGGT | CGTGGTGCAG | GAATACCTGC | GCCGCGATTT | 120 |
| CACCGCCGAG | GACGAAATCC | CGGCGGCGGT | AACGCTGGTG | GTGTCGCGCA | TGGTGGCCCG | 180 |
| CCGGCTGCGG | GCCGATGCGG | GTGATGCCGG | CGCGGTGCCT | GATGGCGTGA | CCCAGTTGGG | 240 |
| GGCCTCGGAG | TACCAGGCCA | GTTTCGCGGA | GCCGTTCGTG | TCGACTGGCG | TGTGGCTGAC | 300 |
| CCGGGCCGAC | CGCGCCGCGT | TGGCGCGGCA | TCGACGGGCG | GTGCAGTCGA | TCGCGGTGTC | 360 |
| CTCGGATCGG | ACGCCGCGCA | AGCCGCCCGG | GTGGTGGTGA | CGTGTTCCCG | CGGCGCCACA | 420 |
| AGGTCAAGCA | CATCCCATGC | GTGGGAACGC | AGCTCGACCG | CATGAAGAAC | GAGAAGCCGG | 480 |
| TGTTCGGTGA | GCCGGTCGAA | ATTGCGGTGT | TCGGGTGGGT | TACCCGCCGG | GACGAAACGA | 540 |
| TCCTGGCGGG | ACACGAGGCC | CGCATCGTGT | CGCGGCTGGA | CGTCACAATG | CCGGCCGACG | 600 |
| CGGCAACCGT | TGGGCTGCTG | GACCAGTTCG | AGGTTGCCGG | CGAGCTGTAC | GAGGTATTGC | 660 |
| AGGTCCGGGA | CTACTCGACG | GGCTGGCACG | GCTGGCGGCC | CGGCATGGTG | GTCGAGCTTA | 720 |
| AGCGGGTGAC | CGGGTAGTGG | CCGGCCGGGT | TCGGTTGAAG | TTCCATAAGG | GCGGCTGGAA | 780 |
| CAACCTCGTT | AGCGAGGTAG | TCGAAACTGA | GGGCGTGGAC | CGCATGAAGC | GGGTCGCGGA | 840 |
| CGCGGCGAAT | GAGGCGCTGG | CCCGGTCCAA | GTACCGCGAC | AACAAGACAC | CGGACGGCTA | 900 |
| CCGGGTGGGC | ACCGAGGGTG | ACGGTAAGCA | ACTGGCCAAG | CGCAGCTTCC | GGGCCACGGT | 960 |
| CATCACGGCG | ACCCCGCAAG | CGATGCGCGA | CAACGCGAAG | AACAACACCC | TCGTTAACGA | 1020 |
| GTTCTATCGG | GCGGGGGGCT | GATCGTGTTT | CCGTACATTG | CAAGCGTTTA | CGTCGATTAT | 1080 |
| CTGACCGAAA | AGCTAACCGA | TGCGCGGGTG | GTAAGCGACG | TGCCGGCGAA | GCGGCCGGCG | 1140 |
| CGACTGGTGG | CCGTTTCGAC | TGCGCCGGCC | GGGTCGAGCG | CGAAACCAGA | GGTGCTGTCG | 1200 |
| TGGCGCCGGC | TGGTGTTCCG | TATATGGGAC | CCGGACGAGT | ACACGGCCGG | CACGTTAGCC | 1260 |
| GAGCGGGTGC | GCTGGGAGGT | TGTGCTGTCG | CGGCGGGCCG | GGATCGGCGT | GCGGCGGGTC | 1320 |
| AACGTGATCG | GGGAGCCGGC | CAAGTTGAAG | GACCCCGACG | ACGGGCCGT | GTTCTTCCAA | 1380 |
| GTAACCGCGG | ACGTCCTAGT | ACGTGCCAAT | CGGTAACGGC | TGCAATTCAT | TTAAGCCTGA | 1440 |
| AAGGGGCAAA | CAGTCATGGC | AAACGCCAAA | AACATTTATG | CGGCCGAACC | TACGGCCGCC | 1500 |
| GGTTCGATCT | TCGCGGCGCC | GCTGGGCACC | GAGGGGCCGA | GCCTGCCCGA | CCCGTTCGAG | 1560 |
| CCGCTGGACG | TTGCGTTCGT | GGACCTCGGC | GACGTGGGCG | AGGACGGGTT | CAACGAAGTC | 1620 |
| ACCGACCGGC | AGATCGACAA | GAAACGCAAC | TTCGGCGGCA | AGGTCGTCAA | GGTTCTCCAG | 1680 |
| ACCCAGTTCG | GCAAGACCAT | CGAGCTGGTG | TTCCTGGAAT | CCCTGAATGC | TGACGTACTC | 1740 |
| AAGGCGATTC | ACGGCGCTAG | A | | | | 1761 |

(2) INFORMATION FOR SEQ ID NO:2:

(i) SEQUENCE CHARACTERISTICS:
  (A) LENGTH: 6611 base pairs
  (B) TYPE: nucleic acid
  (C) STRANDEDNESS: double
  (D) TOPOLOGY: linear (ii) MOLECULE TYPE: DNA (genomic)

(ix) FEATURE:
  (A) NAME/KEY: misc_feature
  (B) LOCATION: 390..1538

( D ) OTHER INFORMATION: /function="coding sequence"
/ product="DNA polymerase"

( i x ) FEATURE:
( A ) NAME/KEY: misc_feature
( B ) LOCATION: 2107..3132
( D ) OTHER INFORMATION: /function="potential open reading frame"

( i x ) FEATURE:
( A ) NAME/KEY: misc_feature
( B ) LOCATION: 3138..3359
( D ) OTHER INFORMATION: /function="potential open reading frame"

( i x ) FEATURE:
( A ) NAME/KEY: misc_feature
( B ) LOCATION: 4690..5028
( D ) OTHER INFORMATION: /function="potential open reading frame"

( i x ) FEATURE:
( A ) NAME/KEY: misc_feature
( B ) LOCATION: 5028..5375
( D ) OTHER INFORMATION: /function="potential open reading frame"

( i x ) FEATURE:
( A ) NAME/KEY: misc_feature
( B ) LOCATION: 5375..5653
( D ) OTHER INFORMATION: /function="potential open reading frame"

( i x ) FEATURE:
( A ) NAME/KEY: misc_feature
( B ) LOCATION: 5653..5910
( D ) OTHER INFORMATION: /function="potential open reading frame"

( i x ) FEATURE:
( A ) NAME/KEY: misc_feature
( B ) LOCATION: 6078..6491
( D ) OTHER INFORMATION: /function="potential open reading frame"

( x i ) SEQUENCE DESCRIPTION: SEQ ID NO:2:

| | | | | | | |
|---|---|---|---|---|---|---|
| GCTAGCGACA | TTCAAACGAT | GGTCCGGGGG | GTGCGCGCCG | AGGTTCACGA | CGAAGCGCAG | 60 |
| CGGCGCGCCG | CCACCGACGA | CCGGCTGCTG | GCCGAGTTGG | ACGCCGAGCG | GGTGCGGTCC | 120 |
| ATCGAGGCCG | ACGCGGTGCT | GCGGCGCGAC | CTGGACGCGC | TACGGGAGGC | CGGCTGACAA | 180 |
| TTCCATAGGG | GCCGCAATGG | TGGTCGACCG | CCGACGAAAA | CCGCACGCGG | TACCGGCGGC | 240 |
| ACGCGAGTTC | GATTCTCGCC | GGCTCCACTA | CGACAGGCGG | GGGTTGCCCG | TCAACCACGA | 300 |
| AACGTGACAG | CGACAAATGG | TAGGCGCTAG | TCTGGCGGCA | AGGTGGCTGG | CCGGCGGGGC | 360 |
| TGGCCCGCGA | CAGACGGGAC | GGGCGTCTGG | TGTTGGGGTT | CACGGTAGGC | AGGGCAGAGT | 420 |
| TCGCGGACGC | GGTGTCGGCG | GTGGGTCGGG | TGTTGCCGGC | GCGTCCGCTC | AACCCGGTGT | 480 |
| TGGCGGCGGT | GCGCTTGGTG | GGTGACGAGT | CCGGGCTGAA | AGTTGAGGCG | TTCGACTACG | 540 |
| AAGTGGCGGC | CGCGGCGACG | GTGGACGGCA | CCACGGTGGC | CGAGGGCGGC | GAAACGCTGG | 600 |
| TGTCGGGCCG | GCTGTTGGCG | GCGATCGCTA | AGGCGTTGCC | GAAGCGGGTG | CCGGTGAAGT | 660 |
| TTACGCACGA | CGGTGCGCGG | GCTGTGGTGC | AGGCGGGGGC | CGCGGAGTTC | ACGCTGCCCA | 720 |
| CGATGGACCC | GCGGGAGTTC | CCGCAACTGC | CCGGCCTGCC | CACCGAGGCG | GGCATCGTGG | 780 |
| ACGGCGATCT | GCTGGCCGAG | GCGTTGGCGC | AGGTGTTGCC | GGCGGTCCAC | ACGGAGGGCA | 840 |
| ACGTGCCGGC | GATCGCGGGT | GTGCAGTTCG | AGTTCGGCGC | CGACGTGCTG | GTGTTGCGGG | 900 |
| CAACTGACCG | TTACCGGGTG | GCGGTGCGGG | AGGTTCCGTT | CACGTGGTCG | GCTGGCGCGA | 960 |

| | | | | | |
|---|---|---|---|---|---|
| CGGCCGAGGT | TGGCACGCGG | GTGACGGTGC | CGACGCGGGC | GCTCGGCGAA | GTGGGCCGGC | 1020 |
| TCGGAGACGG | CAGCATCGCG | GTCGGGTTGG | CGGGCACGCT | GAGTTTGACG | GGGCCGGCGC | 1080 |
| TGTCGGTGGT | GTCGCAGTTG | GTTGGCGAGG | ATTTCCCGGA | CGTGTCGCGG | GTGTTCCCGG | 1140 |
| CCGAGCACAC | CGCGGTGGCG | GTGTTCGATG | CCGGCGAGCT | GGCCGAGGCG | CTGGGCCGGG | 1200 |
| TGCTGGCGGT | GGGGCAGGAC | CCGAAGGCGC | CACGGGTGTC | GCTCGGGTTC | GCGGACGGTG | 1260 |
| CGCTGCTGGT | GTCGGGTGCT | GGTGACGCCG | GCAGCTACCG | GGAGGAGCTG | CCGATCGAGT | 1320 |
| TTTACGGCGA | GCCGGCTGAT | GTGTGGCTTA | ACCCGCGCTA | TCTGCTGGAC | GGCCTCGGCG | 1380 |
| CGGTGAAGGC | TGGGCGGGCG | GCCCTCGGTT | TGGGTCGGCC | GAAGCGGCCG | CTGCTGTTGG | 1440 |
| CTGACGCTGG | TGCGGCCGGG | GAGCTGAACG | TGGCCGGCCC | GTTCGCGCCG | TTGGCCGGCG | 1500 |
| AGTTCCTGTA | CTTGCTGATG | CCGGCGCAGC | CCCTGTGTA | GGGGCCGGC | CCCATGTTCC | 1560 |
| CCCCGCCCTC | GGCGGCGTTG | ATTGCTGTTG | CTGGCTGCTG | GCGCCCGTCA | TCGCCCGCGC | 1620 |
| CGCCGCGGAA | TGCCGCTGCC | GAGGCCGGGG | CCTCGATACG | TCACTGTGAC | GGAAAGGTGT | 1680 |
| GCAGATCATG | GGATTAGCGG | ACAGGTTGGC | GGTCGCGGAA | CCGCGCCGCA | GCTACACGGC | 1740 |
| AGGCCGGTGC | ATCATCTGCG | AATGGTACGC | GCAACTGGGC | GAGACAGACC | GGGCCGAGTT | 1800 |
| CGACAGGTGG | ATCGCGGCCG | GCCGATCGCG | GGCGCAACTG | TACCGGCATT | GCGTCGATGA | 1860 |
| AGGTTTGGAC | GCCTCGGAGG | CGGCGTTCCA | GGCGTGTATC | CGTAAGCAGC | ACCGGGCAGC | 1920 |
| GTCGTGAGCT | TAGCGGATCG | CCTACTGGAC | TACCCGGCGG | CCGACGAGCC | GAAGATCACG | 1980 |
| CAGCGCACCG | AGTTTGACGG | CTCGGCCGGG | TTCATTCAGA | CCAGCGCCAC | GCCGGCCGAC | 2040 |
| GACGGCCCGC | CGGAGTACGA | CGAGCTGCTA | CGCAAGTTCG | GTATGACCC | GGCGCAGGTG | 2100 |
| CGGATTGTGG | GGGCGCCGCG | GGTGTCCCGC | TGGGAGGTTC | CGTACCGGCC | GGTTGAGGGC | 2160 |
| AGCGACGAGA | AGGGCAAGCC | GATCCTCGGC | GAGCTGACTA | CCCGCTGGCT | GGCCTCGTAT | 2220 |
| CGGTTCCACA | TTGCGGCGGC | CGCCGGCGCT | ACTGGCGATG | GCGCAACGGA | CCTCGAGGCG | 2280 |
| ATCGTTAAGG | CGGCCCGGGG | CCGGCGGCGG | GCGACGACGG | ATCGGCGGGA | TGACCCGCGG | 2340 |
| CCGCCGCACT | GGTTCGTGGT | GCAGGCCGGG | GACCTACAGC | TCGGGAAGCG | ATCGCGGGAC | 2400 |
| GGCGACACCA | CGCAGATTGT | AGAGCGGTTC | GTGCAGTCGG | TCGAGACGGC | GGCCGCCGAT | 2460 |
| CTGCGGGAGT | GCCGTCGCCG | AAACGCGGTG | GC-TGGCGTGC | AGGTGTCGTT | CCCGGGCGAT | 2520 |
| TGCATCGAGG | GCAACGTGTC | GCAGGGCGGC | CGCAACGTGT | GGTTGACCCG | GGAGACGGTG | 2580 |
| ACCGAGCAGA | CGCGGGCGTT | TCGCCGGCTG | CTGATGTTCG | CCGCGGAGAC | GTTCGCGCCG | 2640 |
| CTGGCCGAAC | GGGTGTGGAT | CGACGTGGTG | AACGGTAACC | ACGATGAGGC | GCAGCGGCAG | 2700 |
| ACGAACAGTT | ACCCGGGCGA | CGGGTGGGCC | ACCGAGGCGG | CGATCGCGGT | ATCGGACGCG | 2760 |
| CTGACCCTCA | ACCCGGCCGC | GTTCGAGCAT | GTCGGGGTGC | GGGTTCCTGA | GAAATGGTCG | 2820 |
| GGTTATATGA | CTGTGCCCGT | TGGTGATTCG | GTTGTGACGG | TGGCGCATGG | CCATCAGTGG | 2880 |
| CGCCGCGATA | AGGCGTTCGC | TTGGTGGGCT | AACCAGGCGA | TCGGGAACCA | TGCGCCGGCC | 2940 |
| GGCGCGCAGA | TTTTGCAGCA | CGGGCACTGG | CACGAGTGGA | TGGTGCGGAG | TAACGCCGAC | 3000 |
| CGGACGGTGG | TGTGCTCGCC | GACGTTTGAC | TGTGGCTCCG | ATTGGTTCCG | GAAACTGAG | 3060 |
| GGCGGCACGT | CGCGGCGCGG | CGCGGTGACG | TATCTGCTGC | GGGCCGGCGA | GATTTCGAGA | 3120 |
| ATGGGGATCG | CGTAGCCGTG | CGGTACGAGG | ACTGGGGCTG | GCTGGCGGTG | CTGGGCGTGG | 3180 |
| TGGTGGCGGT | TGAGGCGAAG | GCCCCGCCCG | GGCAGATGCT | GTCGCACGGG | GCGGCGCGCT | 3240 |
| ACAAGGCGGC | GCAGCCGGTG | TTGACGTACG | CCGTGGTGCT | GTATCTGGCC | GGGCATCTGC | 3300 |
| TGGGCCGGTG | GCCGGCGCGG | TTGGACCCGT | TGTCGGCGGT | GGATAGGTGG | CGCCGACGGT | 3360 |

```
AGGTTGGTAG ACGGAAAAGT TATGGCCCCC GGGGGTGTGT CCCTCGGGGG CCATATTTTC    3420
GTCGGTGGCT AACCGATTTT TGTGGCGGGA ACGACGCCGT AGGGGCGGCC GTTGGCGGTC    3480
CAATTGCTGA ACGGCTTGCT GGACTTGGCG GCTTTGAGGG CCAGCTCCTC GGTGCGGTGG    3540
AAACTGCGGA TGCGCTTGCC CTCGCCGTCG AGCAGGTCGA ACCAAAGGGC GGCAGCGTAT    3600
TCGTGCTTCG TGCCGCGGGT GGCGGTGTCG TTGCCGTCCG GGTGGTGGC TTGGTAGCGG     3660
TTCATGGTGT CCTCCGTGGT CGTCCCTGCC TTATGTAGAC CAGTCTACAC GCTTGCGGGT    3720
TGTTGTCAAC ACGCTAGGCA GTGGACATCA TGCGACGGAC CCACCCGTTC GACAACCGTT    3780
TCACGGCCCG GTTGACGGCC GGCGCGGCCG GCCCCGGCTG GTCGTCGCCG CCAAGGATCA    3840
GGGCGACCGT TTCGGCGATC GCCTCGGGGT CGATCGCAAT ATGCACGCTG GCGACGGTGA    3900
AGCCCAGTGC CTTAAGGGTG ATGGTCACAG ATCAGTCCTC CCAGTTGACG GAATGGCGGC    3960
CGGGGGTTGA CGTGGTGGCC GACATTACGG CATCGACGTC CGACCAGTCC GGGATTTTCG    4020
AGTACGGCAG CGCATCGAGC ACGCGGCCCG CTTGCGCGGT GTCGCCGCCG AACCATCGGT    4080
CGGCGACCCG CCGGCAGTCG GCGGCCCATT CGGCGCGGAG CTGGTGCCGC GATTTGCCGA    4140
TCACCGCTTG CCGAGCCATC CACGTACCGC CATGCGATCG ACGCCGAGCT GGCGGGCGGT    4200
GCGTTGCTCG GGGTGGCCGG CGGCGATGGC GCGCAACGCG AGGTCGCGGG CGTCGGCGAG    4260
GGCGGCGTCG GCGGCGGCCC GGGCCTCGGC GAGCCGGGCG CCGGCGGCGG CGCACCTTGC    4320
GTCCCAGTTG GGTTCTGCGA TTGTCATGGT TGACACCCTA ACCCGTAACT GTAGACAAGT    4380
CTACCGGCAT TGGGGTAGCG TGTGGCACAT GACGACAGCA CGCTCAACAG TGGACGGGGC    4440
CGCGGGCAGC GGCGCGCCGG TGGTGCGGGG CCAAGAGCTG CACCCGGGCA TGGAGGTGAG    4500
TATCCGCGGG GAGCGGGGTC GGTTCCGCTA CTTGCGGTTT ACGGAGACGG CGGCCGGCGC    4560
GGTGGTGCTC GATTTCATTG GCGGGCCGAC CGGCTACGAG ACGTGGCGGT CGTTCTACCC    4620
TGACCGGGTG GCCCGGGTGC ATAGATCAGC TACCACACGC CGTTATGGCA ACCGAGGGCG    4680
GGCAGTCTGA TGCAGTTGTA TGCGGTAGAC GTGGCCCCTG AGTTCGGGGC GTGGGTTGCT    4740
GGGTTGCGGC GGCTGCGGGT GCAGCAGGTG GTGGATGTGC GGCCGCCATT GCCGGCCGAG    4800
GCCGAGGTTG CGCCGAGGTT GGCGCGGGCG TTGGGGGTGT CGGGGATCAG CTACCGGCGG    4860
GCGCCGTGGG CAGAGTCGGC CGAGCTGGCG GCAGAGGCGG GCGTGTTGCG TTCCGCGGTG    4920
GTGGGCGCTG ATGTGCAGTT GTTGGCGCGT GTGGCGGCCC GCGGTGTGGA TGTGGTGAAC    4980
GTGGGGTGCG TGACGGGCGC GCTCGATTGG TTAGAAGGGG TATCGAGATG ACAGACAAGG    5040
TGTTGGCGCG GATTGTGGCG GGCCTCGGCC TGTTGGGGTT GGCGGGCGTG GTGGCGTTGT    5100
CGGTGGCGGC CGGTGCGGCG CGTGCCGACG AGCCGGGGCC GGTGTTGCCG ACGTATGGCG    5160
AGGGCAGGC GTGCGAGCAG GCGTGGGTGC AGTCGGCGCC GAACGACCCG CGGGTGTCCA     5220
TGAAGCGCGG GCTGGGGTCG GTGATGTATT ACGCCTGGGT GCAGGCGCAG TGCAACGGGC    5280
CGGATGCGAA GTTCCCGAAC GGGGCCGCGG TGGCCGGTTC TGGCTTGGAG CCGGTGTTGG    5340
CGCCGTGGCA GCAGTTGCCC GTAGGTGGTG CCCGATGACT GGCTGGGAAG TGTTGGCGGC    5400
TGTCGCTAAT GAGGAGCCAC ACGGGAAGTT CGGTCGAGAC GCCCACTTCA TCGCTGCGGC    5460
GCTGATCGAG CTGGTACGGA CAGCCGAGGG TAACGCGGAG CAACTGCGCG CCGAGGTTGA    5520
GCGGTTGAGG GGTGCGCTCG ACCGGGTTGT GCAGCTATGG AAAGCACAGA CGTTGACGCT    5580
GATCCACGGC GAATACCGCG CCGCGTTAGA CGATCACGTT AAGGTCATCG AGGCCGTGCT    5640
GCGGGGTGAC CAGTGAAGCG ACCTGTGGCC GAGCGGTTCT GGGAAAAGGT CGCGACCAGG    5700
```

-continued

```
CGGGCGCCGG  CCGGTGGTAT  CCGTGAGGCG  TTGGCCGGCG  GGCAGTTGCA  TGCGCGGCGG    5760

GCGTGGCTGC  CCGCCGGCCG  CCGACTGGCA  GCGTGCACCG  ACACGCGGGC  GGTTGCCGAG    5820

CTGCTGCACG  AACATGTACT  GCCCGATATG  ACGCGCTGGA  CGGGGCGGTG  CTCGGCGGCA    5880

TGGGCCGCAA  GCGCAAGGGC  GTGCTGTATT  TGACGGTGAC  GGCCGGCGAT  GGGGCGGTGC    5940

TGGTGGCCGA  GGTTGGCCGC  AAGGATGAGA  CGGCGGCGCG  TGAGTTCGCG  GCACGGTTCA    6000

ACACTGTGTC  GTCCGGTAGT  TGACAGCACA  ACGTGCGGGG  GTTGACGTTA  CCACCCGCCG    6060

GCTGTAGAGT  GGTCTACATG  AACAGCGCAA  CGATTACCCC  GGCCCACAAG  TTCATTGTTC    6120

GCGGCCGCAC  CGATGAAGTC  ACGACCTGCG  AACTGTGCGG  CCGCGAGGAC  CTGTCGCACA    6180

CGATCGCGCT  GGAAGTGCTG  GACGCGGACG  GCAACGGCAC  TGGGGAGGTC  ACCTACTACG    6240

GTTCGGAGTG  CGGCGCCCGC  GCCGCCGGCT  GGACTGCCCG  CGAGTTCCGC  GCCAACGTCA    6300

AGGCTCACGA  CACCGCGGTG  CGGGACTGGC  TGCGCGCAGA  GCGCGAGTTC  GCGGACGACC    6360

AGTACCACGC  CGCACGGGAT  GCGTGGTTGC  TGGATAACTA  CGGCGTTGCC  GACTTGCACG    6420

CGGCCGCGAA  ACTGGCCGGC  TGCAAGTTCT  ACGCGCTGGT  GGTCGCGTTC  GAGACTGCCA    6480

CCGGCCGGCG  CTAAATCGGG  CTGGCCGCCG  GGTTCCACCA  CGGCGGCCCC  GGCCCCCGTA    6540

CGCCCGCCCG  GCAGCGCTGG  GCGGGCGTTT  TGTTGGTTGC  GTCGTGTTGC  GTTGTGTGGC    6600

GTTTTGCTAG  C                                                            6611
```

(2) INFORMATION FOR SEQ ID NO:3:

(i) SEQUENCE CHARACTERISTICS:
    (A) LENGTH: 15664 base pairs
    (B) TYPE: nucleic acid
    (C) STRANDEDNESS: double
    (D) TOPOLOGY: linear (ii) MOLECULE TYPE: DNA (genomic)

(ix) FEATURE:
    (A) NAME/KEY: misc_feature
    (B) LOCATION: 222..425
    (D) OTHER INFORMATION: /function="potential open reading
      frame"

(ix) FEATURE:
    (A) NAME/KEY: misc_feature
    (B) LOCATION: 451..747
    (D) OTHER INFORMATION: /function="potential open reading
      frame"

(ix) FEATURE:
    (A) NAME/KEY: misc_feature
    (B) LOCATION: 747..1109
    (D) OTHER INFORMATION: /function="potential open reading
      frame"

(ix) FEATURE:
    (A) NAME/KEY: misc_feature
    (B) LOCATION: 1109..2014
    (D) OTHER INFORMATION: /function="potential open reading
      frame"

(ix) FEATURE:
    (A) NAME/KEY: misc_feature
    (B) LOCATION: 2034..2747
    (D) OTHER INFORMATION: /function="potential open reading
      frame"

(ix) FEATURE:
    (A) NAME/KEY: misc_feature
    (B) LOCATION: 2747..3109
    (D) OTHER INFORMATION: /function="potential open reading
      frame"

( i x ) FEATURE:
    ( A ) NAME/KEY: misc_feature
    ( B ) LOCATION: 3109..3444
    ( D ) OTHER INFORMATION: /function="potential open reading
        frame"

( i x ) FEATURE:
    ( A ) NAME/KEY: misc_feature
    ( B ) LOCATION: 3444..3728
    ( D ) OTHER INFORMATION: /function="potential open reading
        frame"

( i x ) FEATURE:
    ( A ) NAME/KEY: misc_feature
    ( B ) LOCATION: 3731..4855
    ( D ) OTHER INFORMATION: /function="potential open reading
        frame"

( i x ) FEATURE:
    ( A ) NAME/KEY: misc_feature
    ( B ) LOCATION: 4855..5376
    ( D ) OTHER INFORMATION: /function="potential coding
        sequence"
        / product="L5 gp37 homolog"

( i x ) FEATURE:
    ( A ) NAME/KEY: misc_feature
    ( B ) LOCATION: 5382..5747
    ( D ) OTHER INFORMATION: /function="potential open reading
        frame"

( i x ) FEATURE:
    ( A ) NAME/KEY: misc_feature
    ( B ) LOCATION: 5837..6307
    ( D ) OTHER INFORMATION: /function="potential open reading
        frame"

( i x ) FEATURE:
    ( A ) NAME/KEY: misc_feature
    ( B ) LOCATION: 6403..7770
    ( D ) OTHER INFORMATION: /function="potential open reading
        frame"

( i x ) FEATURE:
    ( A ) NAME/KEY: misc_feature
    ( B ) LOCATION: 7770..8006
    ( D ) OTHER INFORMATION: /function="potential open reading
        frame"

( i x ) FEATURE:
    ( A ) NAME/KEY: misc_feature
    ( B ) LOCATION: 8033..8236
    ( D ) OTHER INFORMATION: /function="potential open reading
        frame"

( i x ) FEATURE:
    ( A ) NAME/KEY: misc_feature
    ( B ) LOCATION: 8244..9443
    ( D ) OTHER INFORMATION: /function="potential open reading
        frame"

( i x ) FEATURE:
    ( A ) NAME/KEY: misc_feature
    ( B ) LOCATION: 9450..10244
    ( D ) OTHER INFORMATION: /function="potential open reading
        frame"

( i x ) FEATURE:
    ( A ) NAME/KEY: misc_feature
    ( B ) LOCATION: 10371..10586
    ( D ) OTHER INFORMATION: /function="potential open reading
        frame"

( i x ) FEATURE:
    ( A ) NAME/KEY: misc_feature
    ( B ) LOCATION: 11115..11786
    ( D ) OTHER INFORMATION: /function="potential open reading
        frame"

( i x ) FEATURE:
    ( A ) NAME/KEY: misc_feature
    ( B ) LOCATION: 11917..12741
    ( D ) OTHER INFORMATION: /function="potential open reading frame"

( i x ) FEATURE:
    ( A ) NAME/KEY: misc_feature
    ( B ) LOCATION: 12748..14499
    ( D ) OTHER INFORMATION: /function="potential open reading frame"

( i x ) FEATURE:
    ( A ) NAME/KEY: misc_feature
    ( B ) LOCATION: 14771..15154
    ( D ) OTHER INFORMATION: /function="potential open reading frame"

( i x ) FEATURE:
    ( A ) NAME/KEY: misc_feature
    ( B ) LOCATION: 15154..15426
    ( D ) OTHER INFORMATION: /function="potential open reading frame"

( i x ) FEATURE:
    ( A ) NAME/KEY: misc_feature
    ( B ) LOCATION: 15429..15664
    ( D ) OTHER INFORMATION: /function="potential open reading frame"

( x i ) SEQUENCE DESCRIPTION: SEQ ID NO:3:

```
GCTAGCGTAC  ACGCACAGCG  CTTACCAAGC  AATCGCTCCC  GGGCGCGAAA  TGGCTACCGA     60
CACGCCGGCG  ACACGCCGAC  GATTGCGCTT  GCTAGTTGAC  GGCGGCCGGC  CCGCTGGCAT    120
ATTGATCCGC  AACCCCCCGA  CCCCGGATTC  AACTGGCACA  CAGTGGGTGT  CGGGCGGGCC    180
GACAAAGTAA  GTAAGCGGCG  GTTCAACAAC  TGGGAGACGC  TATGACTAGC  GACACAACGA    240
CAGTGGGGCC  GGTGCTGCTG  AACAAGCGGG  ACGCGGCAGC  AGCACTCGGC  GGGATATCTA    300
TTCGACGGTT  GGACACCTTG  GTGCGCGACG  GGCGCCTAAC  GCCGGTGATG  CTCGGCGCCA    360
CCGTGATGTT  CACGCCGGCC  GAGCTGGCGC  GGTTCGCCGA  CGAACTGCCC  TCATGGGAGC    420
CGAAGTGATT  AGGGCGGCCG  CGGAGCGGCT  GTGCGCTGGA  AAACTGCGGA  AGCGGGCCGA    480
AGCTGCCGAA  CGGGCGGCGG  CCGACTGGCA  AGCACTGTGC  CTGAACTTGG  CAGAACGGAA    540
CATGCGGCTG  CGGCAGGCCA  TCGGCGGCGT  GACGCCGCCG  GCGGCCGCCG  ACGCGGCACT    600
GCTCGACGCA  CCGAGGTGGT  TGCTGTGAAA  CCGCTACCGG  AACACGACAA  GCGGGCATGG    660
ACGGCCGGCG  ACTGGGCCGG  CGTGGCGCTG  CTAATGGCGA  CATCGGCCCT  ACTCGGGTGG    720
GCGGTCTACT  GGGAGGCGGT  GCTCGCATGA  TCCGCGCAGC  AATCGCAATC  GGGCTGGCCG    780
CCGTCGCTAT  CGCGGCGGCC  GGCCCCGCCG  GGGCAACACC  GCAACAGGAC  GGCACGTTCC    840
TGTACTTGCT  CGGCGAGGCC  GGGTTCGGCT  ATGAGCAGGC  CGGCCCGGTG  ATCGTCGCAG    900
GCCACACCGT  GTGCCAAGCC  CGCGATGCCG  GCATGACACC  GTATCAAGTG  GCACACGTCA    960
TCGCATCAAA  CACGGGGCTG  ACTGTCTCGG  AGGGATGGCG  GTTCGCGGCG  ATCGCCGCTG   1020
GCGTGTACTG  CGGCGACAAG  GGGTGGGAGA  ACAACCCGCA  CCGCCCGCCG  ACCGGAGACG   1080
GCCCCGCGAA  ACGGGTGGGG  GTGCTGGCAT  GAATGCCCAA  GCAGCCGACG  CGATGATGCG   1140
CCGCCGGCAG  CGAGTCGGCG  AGCTGGCCGC  CGCCGGCCGG  GACCGGCTGA  CGATCGCCCA   1200
CCAGCTCGGG  GTGAGCGTGC  GGACAGTGGA  CCGTGATCTG  CGGGCGCTGC  GGGGTGGCAC   1260
CGTGGCGGCC  CGGGCGCGCA  ACGACGACGC  GGAGAAAGCA  GCGGCGAAGG  CCGCGCAGCG   1320
GGCCGAGGAG  GCCCGTGCCC  GTGGGCTGCG  CCGCAAGCGG  GTCGCCGAGC  TGACCCGCCG   1380
CGGCTGGTCG  GTAGCCGAGA  TCGCCGAGGC  GGTTGGGGTG  TCACCGAACA  CGGTGGTCAA   1440
```

```
TGACCGGGTG GTGACCGGCG CCGTGGACCG CCGGCCGAAG ATGACCGCGG CCGAAGTAGC   1500
GGAAGCCGAA GCGCTGCTGC GTGGTGGCCT CACCTACAAC GAGGTGGCGG CGCGGCTGGG   1560
CCGGCACCAG CGGACGTTGG CGGCCCGGTT GCCGGGCTAC CGCTACAGCC ACCGTGCGTC   1620
CGATGAGCAG ATCGCGGCAC GCCGGCAGCG GGTGCGGGAA CTGACCGAGC GCGGCGACAT   1680
GACGACACGC GAAATCGCCG GCGTGCTCGG GGTGTCGGAG TCGGTGGTGG TGTCGGATCG   1740
GATTCGCACC GGCACCGCGA AGCGGGCCGC GGCGCCGCTG ACCGCCGACG AGCAAGCGTG   1800
GGCGCGGGAA CTGCTGGACG ACGGCGCCCC ATACGCCGAG GTTGGGCGCA CCCTCGGTCG   1860
ATCCGACGCC GCGATCCGGC GCCGGTTCCC GGGATACGAG CTGGACGCCA AGCAGGCCGC   1920
CCAGGTGGCG GGCTAGTCC GGGCGATGAG CCGGATTGAG AAGTTGTCCG ACCCGCTGCG   1980
GGTGACGGCG CAGCAACGAC GCGAGATTTT CCGCTAACCA ACAGGAGGAC ACAGTGACCA   2040
ATGTGATCAG CTTGCCGGGC GCCGACACGG CGTCGGCAGC ATATGACCGG GCGGCAGCCG   2100
ACCGGGCGCG ACGGTTCAGT TTGACGGGCG GCAAGGCGGT CGACGTGCTG GCCGAGCACC   2160
GGCCGGCGAT CATCGCCGAT GGCGTCCGCG AGGCGGCAGT GGCCGCATAT CTGCGGGTGA   2220
GCCGTGAAGT GTTGTCGGTG CTGACTGTTC AGCACCGCGA CGAGCTGACC GAGGCCGGCT   2280
ACGAGTACGC GGCCGGCCTG TTCTCGCGGC GGGCGATCCT GCACGTTGCG CTGCTGCTGG   2340
CGCCCGGGCA GTCCGACCGG GCCGACATGC TGCGGCGCAC CCTCGGCGAC TGGGCCAGCG   2400
ACCGGCCGTT CCGGCCCGGA TCGGCGCCGA CCGCTGTCGT GACCGAACAC GAGGTGGCGT   2460
GCCGTGACCT GATCGGCAAA GCGTCGGAGT TGGTCGAACA AGTCCACGAC GGCGATGCCG   2520
GGCAGGCGTG GGCCGACCTC GAAGCGCTGG ACCGGCACAC GCTGCAAGGT CTGGCGGTGG   2580
CGCTGGCAGC GATGGTGAAC ACCGAGGAGC CGGTGCTGCG GCACTGCCTG ATCCGTGCCG   2640
GGCTGCGGGC CGGCGAAATC GAGGGCGTTG CGGTGCACCC GTCACGGGCG CCGCGTTCG    2700
GTCTGGCCGC GTTGGTGCCG ACCGCCGGCG CCGAGGCGGT GACCTCGTGA AGTTCATCGA   2760
CTCGACAGAC GCGGCGCCTC GGCTCGAACT GACACGGCGC AACCTCGAAA CGCTGCTGGC   2820
GAAGCTGGAC GACCCGCTCA GTGGCCGAAC GCTGATCGCG CCGGGCGGTG AGCTGTGGGT   2880
GACCGCGGTG GAGAGTCGCG CCGGCCGGCC GCTGCCGCGG CAAGCGCACA TAGACCGGGA   2940
GGACCTGACG CTGCTGCTGT CCGCGCTGGA CGAGGGAGAC CCATGCTGGG CGCAGCTCAC   3000
GGTGCCGTTC CGGCACGGCG CGCTCGAAGT GGCCGCGGTG GAGAACGACG CCCACTACTC   3060
CGACCGGCCG CCCGGCCCGA TCTACATGCC CAGCACGGGG GTGACGTTGT GACCGGCCAA   3120
GTTGTCATAC CGGACGCGCA TACTGGTCAA GTGGCAGACG CAGAGCGGGA GCCGGCGCCG   3180
CGCCGGCGGT TGCACTACAA CGACGACCGG GTGGAGCACA TCATGGGCCG CCGGCAGTGG   3240
ATCGGCCCGT GCCGCCGCGG CATGTTGTGG CGGCCCACGC ACGCCGAGTA CGACCTCGAA   3300
ACCGACCGCA CCACCGTTGT TTTCGCGCCG GTGGCGCCGC ACGAAATCGA CCGGGTTCCC   3360
GGGCTGCGGG AACGGCTCGA AGCAACACAG ATGGCCGAGG CGGCGCGGGC TGGCGCTGTC   3420
TCTCACACAG TAAGGAGCGG GCAGTGACTA GTCACATTGA GCAGGCGAGG TTCGCGGCCT   3480
CGCTGGCGTC CGCGGAGGAC GCCGCCGACA TCGGCGCGGT AGTGCAGCGC GGCATTCTGC   3540
ACGCGCTGCT GGCGATCGCC GAGGCGGTCA CCCCGCCGGT TCCGCGGGTG GACATGTCGA   3600
TGCATGTGCC CACGCGGGTC CCGACGCTGG CCGAACTGTC GCGGGTCGGC CTCGAACACG   3660
TCGGGGTTGC CGACGACGAC GAGCCGCTGA TCGACGCGGA CGGGCACCAC TACGACAAGG   3720
GGCTGTGCTG ATGATCGCCA CCGCAAACGA CGGTATCGAG CGGGACCGCT GGGGCCGGCC   3780
```

-continued

```
GAAGATTTAC CCGAAGCCCG GCCGCGGCAA AACGCACGCC GACGTGATCG CCTCAAAGCA      3840
CCGGACGCAC CAGCCAAAAG GGTACCGGCG AACCACCACG TTCATCAGCA TTCTGGAGGA      3900
CCGTTACGCC CTCGAACAGT GGGCGCAGCG CATGGCGATC GCCGGCACAG TACGCAGTGA      3960
GGACCTGACC GCCCGGGCGC TGGCGGCCGA CCCCACCGAG GACCGGGACG CCCTCAACGC      4020
GATCGCCCGC GAAGCGCTGG ACGGGATGCG AACCAAGCTC AAGGCCGACA TGGGCAGCTA      4080
CCTCCATGCT TGCACCGAGC ACCTGGACCG CGGCGGCAGC CGGTCAGACC TGTTGCCGCC      4140
GGCCGAGTGG GCCAGCCTGG CGAGCACCGA CCGGCAGGCA TACGACCTGC GGACGACGA      4200
CTACCCGCTG GCCGACCGGG ACGCCGACCT CGACGCCTAC GACGACGTGA ACGGCGGTA      4260
CGGGTTGCGG TTCGCCACCA TCGAAACGAT GCGGGTGTTC GACCCGTGGG AGGTTGCCGG      4320
CACCCCGGAC AGGACAGGCA CCGGCACCGA CGAGCGGTTC GGCAACAAGT GGCTGGTGCT      4380
CGACCTCAAA ACCGGGGGCG ACTTGGACTA CGACAACACC AAGCGAACGC ACGCCATGCA      4440
GCTAGCTATG TACGCGCACA GCACCGCGTA CACCGCGGCC GAGGGCCGGC ACGACGACGT      4500
GCCACCGGTC AACCGGGACC GTGGCGTGAT TATCCACCTG CCGGCCCGCA CCGGGCAGGC      4560
TGTGCTGCAT TTCGCTGACC TCAAACGCGG CTGGGCGGGT TGCGTTGCCG CGCAACGGGT      4620
GTGGGAGTGG CGCAAGGAGC GGGACATGCT GACCAAGGTG GACGAATGGC AGCCGGCCAA      4680
CCATCTGCAA AAGCTGGCCC TTAACCCGTC GTTCGCCGAG GCCGCGGCCG CGGCCGGCAG      4740
CAAAGACGAG CTGCGGGAGC TGTGGGCGAG GGCATACAAG TCCGGGCCGG GCGTGCTGAA      4800
CGACGGGTTC AAAGCAGCAG TGAAGAAACG GCTAGCAGAA TTGGAGGCAG TGGCATGACC      4860
GAGCACCACA TCGAGGACGT TGGACGGTT GGCCCGGGGG TGGGCGGCGG CGGGGTGCGG      4920
ATCGACGTGC CAGGGCCGTT GACGATGACC ACCACGGAGG CGCGGGCAGT CGGCAGTGCC      4980
CTGCACTCGG CGGCCGCCGA GGCCGACGCC GCCGAGGCGG CCCGAGACGG CGCCGGCACC      5040
CTCGACGGAT ACCAGCAGGT GGCCGCCGAG ACGGCGATCT ATCCGGGCGC CGGCTACGCC      5100
GGCAGTTGGG TGGGCTGTC CTACGTGGCG CTCGGCCTGG CCGGGGAGGC CGGCGAAATC      5160
GCCAACAAGG CAAAGAAAAT CATCCGCGAC AACGACGGCG CCCTGTCGGA CGACAGCCGG      5220
GGCGCGCTGG CCGCCGAGCT GGGCGACGTG CTGTGGTACG TGGCGCAGAC CGCGACCCAG      5280
TTGGGTTACC GGCTCAGCGA CATCGCGGAC GGCAACCTCG CAAAGCTGGC CGACAGGGCC      5340
GGCCGCGGCA CCTTGCAGGG TTCGGGGGAT ACGCGGTGAT CGTGATGGGC AGCCCGCGGC      5400
CGGCGACCGC GGGCGCCCGG CCGGGCCTGC TGGACGGGTT CGACCCGGTT GGTGTTGGGG      5460
CCGTCGAGGG CACCGTGACC CGCATCCGGC ACGGCCTCGG CGGCGCGGTG GAGGTCGGCG      5520
GGTTCATCAC CGCGGGCGAC ACACTGCACC TGCGGCCCGG CGCACCCGCG GTGGTGCTCA      5580
CCGGCGAGGC CCTGGAAACG GTGCGGGACA CGATGGGCTG CGGCAGTTGC GACAGCACGC      5640
AAGAGGGCCT GGCCAACATG CAGGACAAGC TCGACGTGTT GCAAGCAGAA CACGCGGCCG      5700
CGCTGCGGGA GCTGGAAAAG CTGCGGGCAC AGATCGCCGA ACATCGTTAG TTGTCAACTA      5760
CCAAGCGCAG CAGCGACAAT AGGAACGCGC CACCCGGCCT CGGGTGGTTC GCACAACAGA      5820
TAGGAGAAAT ACACAGATGA GCGACGACCT GTTTGACGAC CCGGGTAGCG CCGACCAGAT      5880
CGACCTCGAG GCGGTGGAGG CCGGCTGCT GCTGGTGAAG CCGCACGAGG TACGGGAGGG      5940
CATCAAGACT GCGTTCGGTG AGAAGGACGC CGTTGAAGCC GACGTGCATG TGCTCGACGG      6000
TGGCGACGCC GGCACCGTCC ACCGCGGTGT CTACCTGTTC CCGCTGGTGC TGATCGGGCA      6060
GTTGAAGGGC AACGCCGGCA CGGGACGGTT CAACCTGGGA CGTCTCGGTA AGGGCGAAGC      6120
GAAGCCCGGT CAGAAGCCGC CGTGGAAGCT GCTGGACCCG ACCAACGATG ACCGGGACCT      6180
```

-continued

```
GGCGCGCCGC TACCTCGCCT CCGACCGCTA CAAGCAGAAC ACGGCTGCGC CTGAGCCGGA    6240
ACCGGTGGCG GCTGCTGCGC CGGCCGGCGG CGACCCGTGG GGTGGCAGCA ACGAGGCGCC    6300
CCCGTTCTAG GGGCTGCGGG ATAACACCGG AGGGCCGCGC ATTCCGGGGT AAGTAATCAC    6360
GCGGCACCAA GCTTTCCCGA CCCGTCAACC ACGAGGCGCA ATGTGATCCA CTACCAAGAC    6420
GAAACGGTGA CGCTGCACCA CGGCGACTGC ATCGACGTAA TGGACGAACT ACCAACCGAT    6480
TCCGTCGACG CGATTGTCAC GGACCCGCCG TACGGCATCC GGTTCATGGG CAAAACGTGG    6540
GACGGCGCCG AGATTGAGCA GCGCACCCGC CGGGGCCGCG AAACGTGCCC GATGCCGGCC    6600
GGGGTCGGCG GCCCACAAGG CGGGTACAGG TCACGGGCCG TCGAAGCTGG CCGCTACGAC    6660
CTGTCTGCCA ACGCGGCCTT CCAAGAGTGG TGCACCGACT GGGCCGGCGA GGCGCTGCGG    6720
GTCGCCAAAC CGGGCGCGTG GCTGCTGTCG TTCGGCAGCC CCCGCACCTA CCACCGGCTG    6780
GCCGCCGGCA TAGAGGACGC CGGCTGGGAA ATCCGGGACG GCATCATGTG GCTGTACGGT    6840
TCCGGGTTCC CAAAATCCCG GGACGTTACC GACGCGATGA ACCGGCACCT GGCCGGCGAC    6900
CGCGGCACCC GGCCCGGGCT GTACGAAGTC ACCGCGTATC TCAAAGCGGC CCGGGACGCC    6960
GCCGGCTGGA CGAATCGGCG CATCGATGAA CTGTTCGGCA CCAACGGGAT GGCCGGGCAC    7020
TGGACCAGCA CGGCTAGCCA GCCGGCGTGT CCCTCGGTGC GGCAGTGGGC CGAGCTGAAA    7080
GCAGCGCTCG CACCACACCT CGGCGACGAC CTGGACGAAC TGGTCGAACA GTTGGCGGCG    7140
ACCGAACGCC CCGAGGACTG GGGCGAAGGT GGCGGCAAAC GGTTCCTCGA CACGCTGCAC    7200
AAGGGCGGCG AGTTCGAGCC GGCCGGCGCG TGGGGCACCA CCCTCAAGCC GGCGTTCGAG    7260
CCGATCGTGG TGGCCCGCAA ACCGATGCCG TGCAGCACGC CCGCCAACAT TCTGCAGCAC    7320
GGCACCGGCG GGCTACACAT CGGCGCGTGC CGGGTCGGCG ATCACTCGTA CGACGGGCAC    7380
CCCGACCGGC AGGGCGGCCG CTGGCCCACC AACGTTCTGC TTGACGAGGC GGCCGCCGGC    7440
GAGCTGGGCC GGCAGCACGC CGACGCGCCC CCGTTTTTTC CGACGTTCCG GTACACCGCG    7500
AAGGCGGCCT CGTCGGAGCG GCCCCGCGTC GGCGACGTGA TGCACCCGAC CGTCAAGCCG    7560
CTGGAACTGA TGCGGCGGCT AGTGCGGTTG GTGACGCCGC CGAATGGTGT TGTGCTCGAA    7620
CCGTTCGCGG GCAGCGGCAC CACGATCGAG GCCGCGCTCG CCGAGGGGAA GCGGGTGGTC    7680
GGCATCGAAC GCGACGACAC CTATCTGCGG CTGATTGCGG CCCGGCTCGG CCGGGCGCAG    7740
CTCGGGTTCG ATTTCGCAGA GGAGACAGCG TGATCACCGT TTACACCACC GGCCCCGGCT    7800
GCCAGCAGTG CGTGGCGACG AAACGGCACC TCGACAAGCT CGGCGTGCCG TACACCGAGG    7860
TCGACCTCCG GGGCGAACCG GAGATCGCCG AGGCGCTGCG GGCCGCCGGC TACACCACGG    7920
CGCCGATCGT GGACGTACCC GGGCAGCCCC GCCCCATCAC GGGGTACCGG CCAGATGAGC    7980
TGGACAAGAT CGCCGCGGCC CTGCGATGAC CGCACACCAA GTAGGCGACC CAGTGTGGGT    8040
CGATTTCGAC GGCGCCGAGC ACCCCGGCGA AGTCCTCAAA GTCGAAGGCG GCGGCTACCT    8100
GCTCTGCATG ATCCACACCG ACCCCGAGTG GGACTACGGC CGCGCCTCGG CCCGCGTGAT    8160
GCCTGAACAG GTTGTCGCCG CACGGATTAC GCACGTACGG CCCCGCACCC CCGACACCGC    8220
CCCCGATGAA AGGACATAGC GCCATGCCTC AACAGATCGA CGGCTATCCG CTGCTCAATT    8280
TCGCCTCCGA AATCGACGCG CTCACACTGG ACCAGGCCAA GCAGACCGCC GGCCTGCCGT    8340
TCGTCCACCC GCATGTGGCG CTGATGCCCG ACGCGCACGC CGGCAAGGGT TCATCGGTCG    8400
GCACCGTCAT CCCGACTATC GACGCCGTGA TCCCGGCCGC GGTGGGCGTG GACATCGGCT    8460
GCGGGATGAT CGCCGCCCGC ACCATCTACA CCGAGGACGA CCTGGACGGC CGGGACCTCG    8520
```

```
CCGCGCTGCG GCACGCCATC GAGGGCGCGA TCCCGCTGTC GCCGGGCAAC TACAACCGCG   8580
ACACCGATCG TTTCCCGTGC ACCGCCGGCC GTATCGCCAC CCTGACCGAC CTCGCCGGCC   8640
GCGGCACGGA CGGCATCCCA GCGGTTGACC TGTCGCACTC ACCGAAGTGG CGGGAACAGC   8700
TCGGAAGCCT CGGCGGCGGT AACCATTTCA TCGAACTATG CCTGGACGAA ACCGGCCGGG   8760
TGTGGCTGTT CCTGCACTCC GGGTCGCGTG GCGTCGGCAA CAAGATCGCC CAAAAGCACA   8820
TCAAGGTCGC GCAGAAACTC ATGGACCGCT GGTGGATTCA GCTCCCAAGC CCCGACCTGG   8880
CGTACTTGCC GCAAGGCACA CCGGAGTTCG CCGACTATCT GCGGGAGCTG CACTGGGCGC   8940
AGCGGTTCGC GCTAGAGAAC CGCGCCGAAA TGATGGACCG TTTCGCTATC GTGTTCGGCG   9000
AGTGGATCGG GCACCCCACC GGCGGGGCGC TGGTGGAAAC CACGGTGAAC ACGCACCACA   9060
ACTACACGAC GCAGGAACGG CACGGCGGCC GCGACGTGTG GCTGACCCGC AAGGGCGCCA   9120
TCGACGCGCA CGCCGGCGTG ATGGGCCTGA TCCCGGGCAG CATGGGCACC CCGTCATACG   9180
TGGTGCGCGG CAAGGGCAAC CCGGCCGGGC TGTGCTCGGC GCCGCACGGC GCCGGCCGCC   9240
GGCATTCCCG CACCCAAGCC CGGAAGCTGT TCACCGAGGC CGACCTCGCC GACCGGATGC   9300
AGGGTATCGA GTACCGGCAC GGGGACGCGT GGGTTGACGA AATCCCGGAC GCCTACAAGC   9360
CAATTCAGAC CGTGATGGCC GACGCCGCCG ACCTCGTGGA GGTTGTGCAC GAGCTGCGGC   9420
AGATTCTCAA CGTCAAGGGC AAGTGAATGA TGTACACGAC GTGCCCAACG TGCCGGGACA   9480
CCCTCGAACT GGCCGACGAC TGGGCGCCGG CCGAGGGTGC CGAGCACCGG CCGCCGGTGC   9540
ACGACGGCTG CCCGCCGGCG CCCCTAACCC CGGTCGATCA GCTGTACGAG AATTTCCGGG   9600
AGCTGGTGGC GAGAATCGCG GCGCCCGACT ACAAGCCGCG CATGGACGCC GGCACCAACA   9660
TGGACGAGCT GAACCTCGAC GCACTCAAAG CGAAGATCGA CCAGCACGAC CAGCAGCCGC   9720
CCCGGCTCGG CGATGCCGCC CTGATCTATG CCTCGTGGGG GTGGCCGGTG TTTCCGCTGC   9780
GGCCGGTCGG CGCGCCGTGC CGCAATGGGC GCCGGGACAA GTGCGCCCGT ATCTGCCAGT   9840
GCCCGAAAAC ACCGGCGACC CCTAACGGAT TCAAGGACGC CACTACCGAC GCCGAACGTA   9900
TCCGCACCTA CTGGGCCAAG GTGCCGGGCG CCGGCATCGG CATAGCCACG GCCATGCGT    9960
TCGACGTGAT CGACCTGGAC CTACCGGACG GGCCGGCCTC GTGGGCAGCC ATGAGCGGCA  10020
AGCTACCCGT ACACGGGCAG GTGCTCACCG GCAACGGCGG CCGCCACCTG TACACCCCGG  10080
TCACGGGCGC GAGAAACGGC GCCCGCATCG CACCCGGCGT GGACTACCGC GGCCTCGGCG  10140
GCTACGTGGT GGCGCCCCCG TCATGGCTCG GCGACCACGG GCACAAGTGG CGGTGGCTGA  10200
CGAAACCCTC ACCGGCACTT ACTGGCCCGT CCACGTCAA CGGTTAAACG TCGCGCCGTC  10260
AAACAGTGGT TGATACCATG ACGTTGCCAG AGATTGCCGT TATTCCGTGG GCCGTGCTCG  10320
CGGTGGCGTT CCTGATCCCG ATGATCCGGC GACGATTGTG AGGCCCCGA ATGCTCGAAA   10380
CCGCGTTACA CCACCCGAAG CTGCACCAGG TCAAGACATA CCCGAATGAT CGGGCCGGCG  10440
GCGGCGCGTT CCACACGTTG ACGCTCACGC ATCGCAGCGC CGCCGACGAC CGGGCCGCCA  10500
TCGTGCTGTT CATCGACCCC CACTGGGCCG AATGGACGC CATCGTGGAC GCCGTAAACG   10560
CCTACCGCGC AAAGCGGGCC GACCGATGAC CGCCAACGAC GACCACCTCG GCCTCACCAC  10620
CTACTGCCCG CCGCCGGCCG CTTGGCACAT TGTGGCCGGG GTGGCGCTGG CGATCGTGGC  10680
ATGGCTGGCG TTCGCGGGGC TGCTGCTGGC CGCTATGTCG TGGGTGTCAG TCCTGTGACC  10740
GCCGCGGCGC CAGGCAGCAC CCAGCCCTGG CTACTGCACA CCAACATCCC GGAGGACCCT  10800
GCCGCGACTG GCATCACCTA CATTGCTGGC CCGATGACCG GCTACCCGGA CCACAACTAC  10860
CCGGCATTCA TGGCGAAGGC CGCCGAGCTG CGGGCCGCCG GCGTGCCGGT AATCAACCCG  10920
```

```
GCCGAGTTCC ACGGCAACGA CCTAGACCAC CCGTGGGACT GGTATCTGCG GCGGGACCTC       10980
GCCCAGTTGG TGAAGTGCGC CCGCGTGGTG TTCCTGCCGG GCTGGCGCGG GTCGCGGGGC       11040
GCCCAGCTCG AACACGATGT GGCGCAACGC CTCGGCCTCG AGCTGGTGTA CCCACCCGAG       11100
GACGGGCCGA GACAATGACG GACACCGAAA TCCTGGACGC CCTCACGCGA GCACTCAACT       11160
ACGCGGACAG CCACATCGAC ACGTGGCCAG CCGACGACCA CCCGGCGCGC GCCGCCGCAT       11220
CGCGGCAGTA CCACGGCCGT TTCATCGCCG AGGCCCGGCG GCTGCTGGCC CGACGCAACA       11280
CCACCACCAC AGAAGGACCC ACCAATGCAC CCCGAGGACA CTTGGACACT GACCGGCCGG       11340
CCCGCGCAAC GGAACGGCG CCGCGGGTTC AAACAGCCGA AGCCGGCCCG GTCACGCTGC        11400
ACCCGGCTCC AACCGCGGGA ACGGCGGCG CGCCGGAAGC CGCCGAGCAT CGCGGGCGCC        11460
AACCGGACGC GGAGGGCGCG TACCGCCGCG TCGATCCGGG CGTGGCTCAA CCCCGCCGCC       11520
GCCGCGTAGG GCTGCCAGCC GACTGCGGCG GCGACTGCTG CCAGCCGGCC CCGACCCGG        11580
CCGAAGCGGC CCGGTACGGG CGGCACGCGG CCGCCCGCAA CCGATCCTGG GTCGCAACCA       11640
CCGAAATGAC CGCCGCACTC ATGGGCGTGC TGTCCGACCA GCGCGTCAGC GGCCGACCAC       11700
CCGGCAAGCA CCGCGCCAAA GGCCCGATCA CGTCGCACCG GCTCGGCGGC CGCATCTTCT       11760
ATTTCCTGCC CGGCTACCGG AGGCCCTGAT GTTCGGGCCG GCAATCGACG CGGCAATGGC       11820
CCGCATACTC ACCGGCCCCA TAACCCACCT ATACGCCGGC CTGTACAGGG CCGGCGTTCT       11880
CACAACCGAC CCCGCCCCCA CCGACAAGGA GACACGATGA GCACCGGCGA AACGATCCAC       11940
ACGAGCAGCA CCGGCGGGCA GAAAGCCGGC AACCACGTAC GGGTCGGGCT GATCCCAACC       12000
GACGAACTGC TAGAAGTGGC CGCCCTGTTC GGCAAGGGCG CCGAGAAATA CGACGACAAC       12060
AACTGGCGCA AGGGCTACCC GTGGCACCTG TCGTTCGACG CCCTGTGCCG GCACCTGTTC       12120
GCATGGTGGG GCGGCGACGA GTTCGACAAC GGCGAGGGCG GCACCGGGCA GGAGCACCTG       12180
GACGCCGTGA TTTTCCACGC GCTGGTACTG AAATGGTTCC GCAAGCACCG GCCGCTGTTC       12240
GATGACCGGC CGAACACGGT AGCGCTTACC GAGGCCCTGC TGGACGCCGC CGACGACGCC       12300
ATGAAAGCGC AAGAGGCCGC CGAGTTCACC GCCGCCACC AGGACGACCA GGACGACAGC        12360
CCCGTGCAGT CCCTCGGCGA CGAGCACCGC GCCCGGCAGT GGGTGGACTC AGACGGCGAC       12420
CGCTGGCGGT GGGACATGTA CGCCGGGCGG TGGCAGTACC GCAACGGCAC CCCGGACGGC       12480
ACCGCCGAGG ACCTGGCATG GATGGACGAC TGGCAGCCTG TCGCCGAGTT CGGCCCCTAC       12540
ACGCCGGCCG TCGAAAAGCT CGGCACCGAC CACCAGGACC GGCAGTGGGT GGACGAATCC       12600
GGCGACCGCT GGCGGTGGGA CGCCGACAGC GAGGAGTGGC AGTGCCGCGT ACACGGCCTC       12660
CCCCACTGGG GACCCACCAC GCTCGGCCCC AACCCGCACG GCCCGTTCAC CCCGGCCCCG       12720
GCAGGCGCCG AGGGAGGCGA ATAGCCGATG ACGGCCGAAA CATTCGACCT CGCAGCATGG       12780
GTCGAAGCGA ACAAGGCCGG CAGCAAGCCG CCGGCCGCGA CGGCCCGGCC GCCCGGCACC       12840
TACACCCCGC CGGCACCACC AGCCGGCGCT GACCGCTACG CCGCCGCGGC CCTCGCCGAC       12900
GAATGCCGCG AAGTAGCAGC CACCACCGAA GGCGGCCGCA ACCACCGGCT CAACACCGCC       12960
GCGTTCAACC TCGGCAGCCT CATCGAAGCC GGCGCCCTCA ACCGCACCCA AGTCGAACAC       13020
GCTTTGCGGG ACGCCGCCCG GGCGTGCGGG CTAACCGAAG CCGAGATCGG CCCCACAATC       13080
GCCTCCGGGT TCCGATCCGC AGCCACCAAG GTCGGCCCCC GCGTCATCCC GGACGCGCCC       13140
CCGGCCCTGG ACCTCGGCAA CACCACCCTC GACCGGGGG AGCTGGACGC CGCGGCCGCC        13200
GGCGACGACG ACGGGGCGCC CCCCGCTGAT GTGCTCGAAC AGCTCGAGGG CGATTTCTGG       13260
```

```
CAGCGCCGGC CGTCCCTCAA CCTGATCTAC ACGGCGGCCC TGTCCCGGCT CGCATCACCG    13320
TGGGCCGTGT TCGCCTGCTG CTGCGCCCGG GTGGTCGCTG ACATCCCACC CACGGTGCAG    13380
TTGCCGGCGA TCATCGGCGG CCGCGGGTCA CTCAACCTGT TGCCGCCAT  ATCGGCGAAA    13440
TCGGGTGGCG GCAAGGGCGC CGCGATGGCC GTGGCCGACG CGCTCACCCC GAACCGCGAC    13500
CTCGAGGTCC GGTCGATCGG TTCCGGGGAG GGAATGATCG AAGCCTACCG GCGGGACACG    13560
AAGAAAAACG GCGGCGACGA CGACGGAATC GACGGCCCAG ACGACAGCAT CGTGACGTCG    13620
ATCCTGTTCA GCATCGAGGA AATCGACAGC CTCGGCGCGA TGGGCGGCCG ATCCGGCCAA    13680
ACCACCATGA CCGTGCTACG GCAAGGGTTC AGCGGCGAAA AACTCGGGTT CACCTACCGC    13740
GGCCGGCAGC ACGAAACCGT GCCAGCCCAC ACGTACCGGA TGACCGTGGT CGCCGCGGTG    13800
CAGCCCGAGC GGGCAGGCAC CCTGTTCGAG GACGCCGGCG GCGGCACCCC GCAACGCTTC    13860
GCGTGGTTCC CGGGCCGCGA CCGGCGCATC ACCGCCGACC CGCCAGACTG GCCGGCCGAC    13920
CGGGCTGGCC AGCCGGCAGT AATCCCACGG CTGTCGAACG ACCACAAAGC GCAAGCGGCC    13980
GGCGTGGTCG ATGTGCCCAA CATTGTGGTG CGAACAGTGC GGGAGGCCCG GCCGCGTCC     14040
ATGTCCGGGG ACGACAACGC GCTCGACGGG CACGCGCTGT TACCCGGGA  GAAATACGCC    14100
TACGCGCTGG CCGTGCTGGA CGGCCGCACC CACATGACCG ACGAGGACTG GAACTGTCC     14160
GGGGTGGTGG CCGCCGTCTC CGATTGGTGC CGCGATAAGG CACTGGAGGG CTATCAGGCG    14220
GGCCGGCACC GCGCCGCGGC CGACCGGGGC GAGCTGCGGG CGGTGGAGGA CGACGAGCGC    14280
AACGCGGTGG CCGCGATGCG GGCCGAGAAG GCGGTGCAGC GGATCGCCGG GCTGATCGTC    14340
AAGCACCTCG GGGATGCCGG CGGGTTCCTG CCGTGGGCGG GGCGCGGTGG CCTGCGGCAG    14400
AAGCTCGGCT CGCGTGACCG GGCGCGGGCC GAGGCTGCTT TGCAAGCCCT CGTAGCGGCC    14460
GAGCGCATCA CGGCGCGGGA TGACGGGTGG GCGCTGAAAT GACGCGCCAG CAAACAGTGG    14520
TTAGCGGGGC TAAGGTAGGA CGTAGGACAT GTTTGTCCT  ACCGGGGGTC GCCGCCAACC    14580
CCCCTCGCTT ACCGGCCGCT CAGAATCCCC CTGCATGTAT AAGAAATTAT TATCTTAATA    14640
TTCAATCGCA CGAAGGCATA TTGGCAGTCC TACGGGTTGC CCAAGTAGGA CGTCCTACTG    14700
TCCTACCGAT TTCGGGCGAA AACGCGCAAA CACCCGCAAG CCAGCAACAC ACGCGACAGG    14760
AGGCCCCATA GTGGCACGCA CCAACCGATC AGCCGCCAA  GCCGGCGCAC GCTTCGAACG    14820
CGAAATCGCC GACTACCTCG CCGACGCCCT CAACGACGAC CGCATCGACC GGCGCGTCAA    14880
ACGAGGCACC AACGACCGCG GCGACATCGG CGGGCTACGC GCCCACGGGC AACGCATCGT    14940
CGCCGAATGC AAGAACACCG CAAAGCTTGC ACTCCCGGCG TGGGTCGCCG AAGCCCACGC    15000
CGAGGCCGGC AACGACGACG CGCTCGTAGG CGTGGTGATC CACAAACGGC ACGGCGTGGG    15060
CGACCCCGGA CGGCAATGGG TCACCATGAC CGTTGACGAC TTCGCCGCCC TGGTGACCGG    15120
GCAGCGCCAC GGGCACCGAC TGGACGTGGC CTCGTGAGCA TCACCGTTCG GCGCAACCTC    15180
AAACAGCGCT GCCCGCTATG CGAAACCCCG ATCCGGGCCG GCGACGAAAT CAACACCGAC    15240
AAACGCGGCC GCCCCATCCA CACCAGCTGC GATGCCGCCA CATACAACCC ACCGGCCGAC    15300
ACTCGGGACC GTCGATCAAC TACAAAACGC GACAGCGACA AACAGCAAAC GTACACTGTG    15360
AAGGGACAGC GCAGCCGAGA ACGGCACTGC ACCGACTGCC ACCTGATCCA CGCAGGGGAG    15420
TGTTTCTAGT GAGCTTGGAC CGGCCCGACA TCCTGGCCGA CCTCGACTTC GAGCCAGAAC    15480
CAGCCCAGTG CGAAGCACTC ACCGGGCCGG CCGGGCAACG CTGCACCGCC CAAGCCACCA    15540
CCTACACCAA GGTCCACGCG CTAGGCGGCT GCCTCGCCGC CGGCCTCACC CCCGATGGCG    15600
GCCTGGTGTC CCTATTCTGC GGCCGCCACG CAGCCGAACG GGCCTGCAAA GTCGGCGAAC    15660
```

-continued

TAGT                                                                                                          15664

(2) INFORMATION FOR SEQ ID NO:4:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Ala Asn Ala Lys Asn Ile Tyr Ala Ala Glu Pro Thr Ala Xaa Gly Ser
 1               5                  10                  15
Ile Asp Ala Gln Pro Gly
            20
```

(2) INFORMATION FOR SEQ ID NO:5:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Ala Asp Val Ser Arg Asn Asp Val Ala Thr Leu Ile Gln Glu Ala Tyr
 1               5                  10                  15
Gly Asp Asp Phe Leu Ser Trp Ala Ala Lys Gln Ser
            20                  25
```

(2) INFORMATION FOR SEQ ID NO:6:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Ile Val Ile Glu Arg Gly Asp Ile Pro Ser Leu Val Xaa Arg Gly Xaa
 1               5                  10                  15
Arg Leu His
```